(12) United States Patent
Shadduck

(10) Patent No.: US 9,717,644 B2
(45) Date of Patent: Aug. 1, 2017

(54) WEARABLE SENSING AND ACTUATOR SYSTEMS, AND METHODS OF USE

(71) Applicant: John H. Shadduck, Menlo Park, CA (US)

(72) Inventor: John H. Shadduck, Menlo Park, CA (US)

( * ) Notice: Subject to any disclaimer, the term of this patent is extended or adjusted under 35 U.S.C. 154(b) by 0 days.

(21) Appl. No.: 14/978,932

(22) Filed: Dec. 22, 2015

(65) Prior Publication Data
US 2016/0175186 A1 Jun. 23, 2016

Related U.S. Application Data

(60) Provisional application No. 62/095,740, filed on Dec. 22, 2014.

(51) Int. Cl.
| | |
|---|---|
| *A61H 9/00* | (2006.01) |
| *A61H 19/00* | (2006.01) |
| *A61H 23/04* | (2006.01) |
| *A61H 23/02* | (2006.01) |
| *A61B 5/11* | (2006.01) |

(Continued)

(52) U.S. Cl.
CPC .............. *A61H 19/34* (2013.01); *A61H 19/40* (2013.01); *A61H 23/04* (2013.01); *A61B 5/11* (2013.01); *A61H 9/0078* (2013.01); *A61H 23/0218* (2013.01); *A61H 23/0245* (2013.01); *A61H 23/0263* (2013.01); *A61H 2201/0214* (2013.01); *A61H 2201/0285* (2013.01); *A61H 2201/1253* (2013.01); *A61H 2201/165* (2013.01); *A61H 2201/1635* (2013.01); *A61H 2201/1688* (2013.01); *A61H 2201/5005* (2013.01); *A61H 2201/5012* (2013.01); *A61H 2201/5043* (2013.01); *A61H 2201/5048* (2013.01); *A61H 2201/5061* (2013.01); *A61H 2201/5064* (2013.01); *A61H 2201/5097* (2013.01); *B25J 9/16* (2013.01); *B64C 13/04* (2013.01); *G05G 9/047* (2013.01); *G06F 3/017* (2013.01)

(58) Field of Classification Search
CPC ........ A61H 9/00; A61H 9/0007; A61H 9/005; A61H 9/0078; A61H 19/00; A61H 19/30; A61H 19/34; A61H 19/40; A61H 19/50; A61H 23/00; A61H 23/02; A61H 23/0254; A61H 23/0263; A61H 23/04; A61H 23/06; A61H 2201/00; A61H 2201/0157; A61H 2201/0153; A61H 2201/02; A61H 2201/0214; A61H 2201/0242; A61H 2201/0285; A61H 2201/12; A61H 2201/123; A61H 2201/1238; A61H 2201/5058; A61H 2201/5064; A61H 2201/5079; A61H 2201/5084; A61H 2201/5097; A61H 2205/087

See application file for complete search history.

(56) References Cited

U.S. PATENT DOCUMENTS 6,368,268 B1 * 4/2002 Sandvick ............... A61H 19/44
                                                                    600/38
6,953,058 B2    10/2005   Fernandes et al.

(Continued)

*Primary Examiner* — Quang D Thanh
(74) *Attorney, Agent, or Firm* — Levine Bagade Han LLP

(57) ABSTRACT

Wearable sensors and cybernetic systems that allow one or more operators to interact and control operations of electronic, mechanical, robotic, or biomedical systems, and methods of use in gynecology, female sexual response and female sexual well-being.

20 Claims, 19 Drawing Sheets

(51) Int. Cl.
*B25J 9/16* (2006.01)
*B64C 13/04* (2006.01)
*G05G 9/047* (2006.01)
*G06F 3/01* (2006.01)

(56) References Cited

U.S. PATENT DOCUMENTS

| | | | |
|---|---|---|---|
| 7,005,493 B2 | 2/2006 | Huang et al. |
| 7,075,162 B2 | 7/2006 | Unger |
| 7,118,910 B2 | 10/2006 | Unger et al. |
| 7,291,512 B2 | 11/2007 | Unger |
| 7,368,163 B2 | 5/2008 | Huang et al. |
| 7,392,827 B2 | 7/2008 | Fernandes et al. |
| 7,476,363 B2 | 1/2009 | Unger et al. |
| 7,640,947 B2 | 1/2010 | Fernandes et al. |
| 7,666,361 B2 | 2/2010 | McBride et al. |
| 7,691,333 B2 | 4/2010 | McBride et al. |
| 7,695,683 B2 | 4/2010 | Quan et al. |
| 7,837,946 B2 | 11/2010 | McBride et al. |
| 8,007,746 B2 | 8/2011 | Unger et al. |
| 8,058,630 B2 | 11/2011 | Pieprzyk et al. |
| 8,104,514 B2 | 1/2012 | Fernandes et al. |
| 8,105,824 B2 | 1/2012 | Facer et al. |
| 8,157,434 B2 | 4/2012 | Cohen et al. |
| 8,168,139 B2 | 5/2012 | Manger et al. |
| 8,206,593 B2 | 6/2012 | Lee et al. |
| 8,282,896 B2 | 10/2012 | Facer et al. |
| 8,343,442 B2 | 1/2013 | McBride et al. |
| 8,389,960 B2 | 3/2013 | Pieprzyk et al. |
| 8,590,573 B2 | 11/2013 | Fernandes et al. |
| 8,591,834 B2 | 11/2013 | Cohen et al. |
| 8,616,227 B1 | 12/2013 | Facer et al. |
| 2006/0106466 A1* | 5/2006 | Decker | H04L 67/125 700/1 |
| 2007/0049792 A1* | 3/2007 | Levy | A61H 19/44 600/38 |
| 2012/0136284 A1* | 5/2012 | Land | A63B 21/00065 601/5 |
| 2013/0109914 A1* | 5/2013 | Imboden | A61H 1/00 600/38 |
| 2013/0190667 A1* | 7/2013 | Kane | A61F 7/007 601/149 |
| 2015/0328082 A1* | 11/2015 | Jiang | A61H 19/00 600/38 |

* cited by examiner

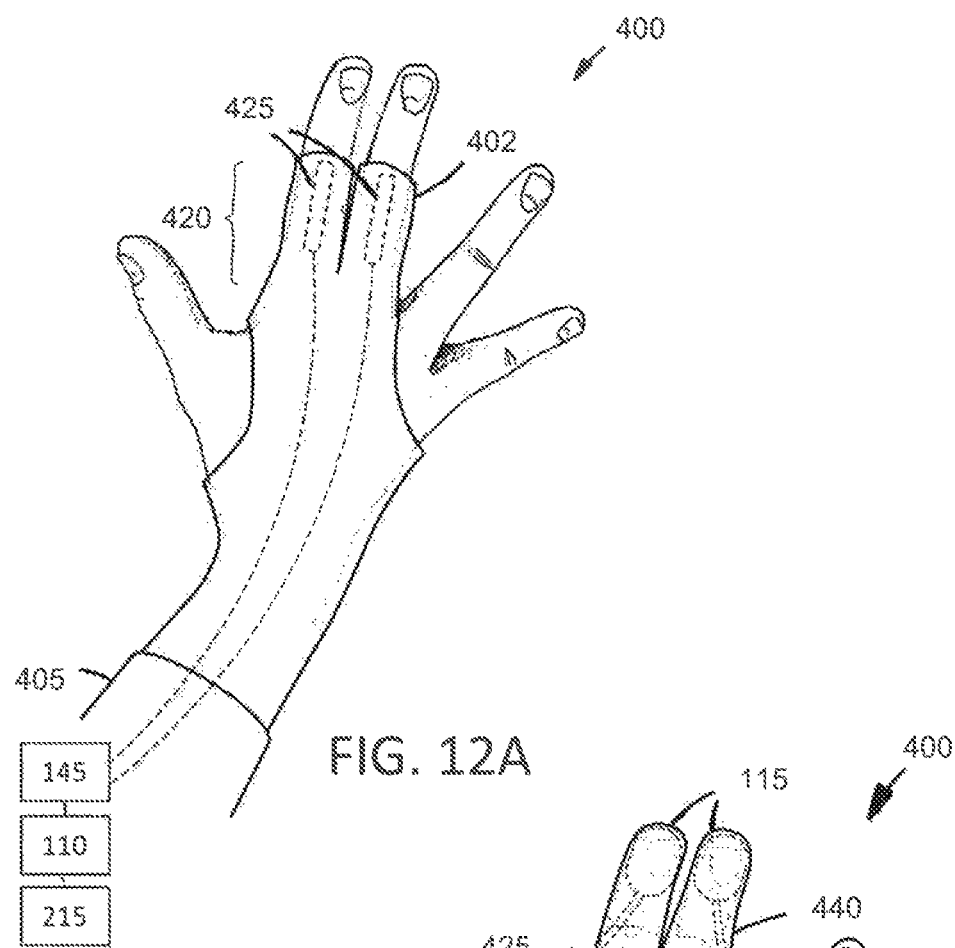
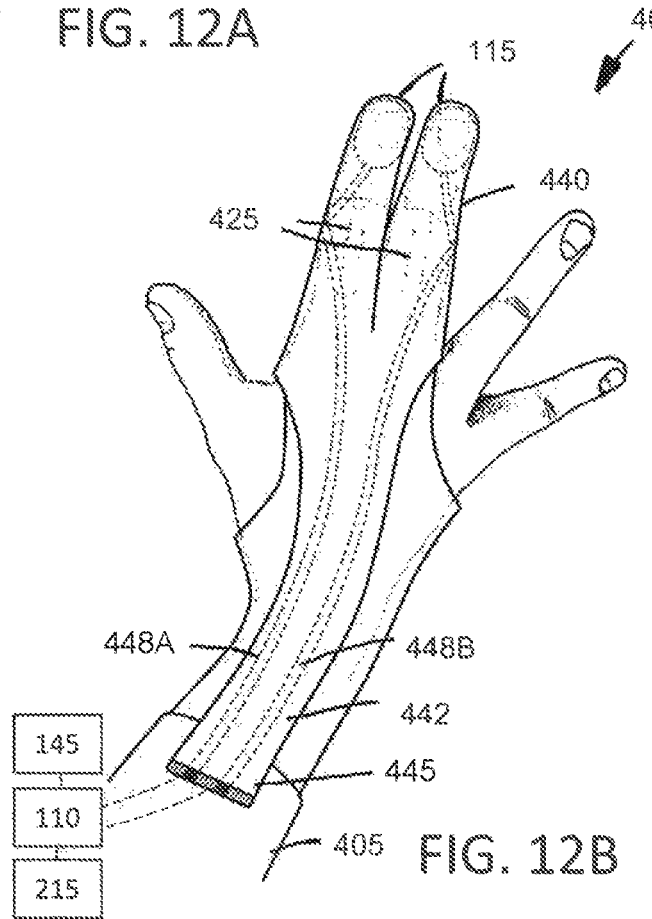

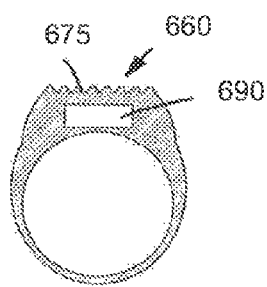 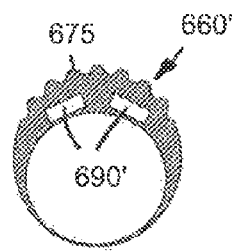 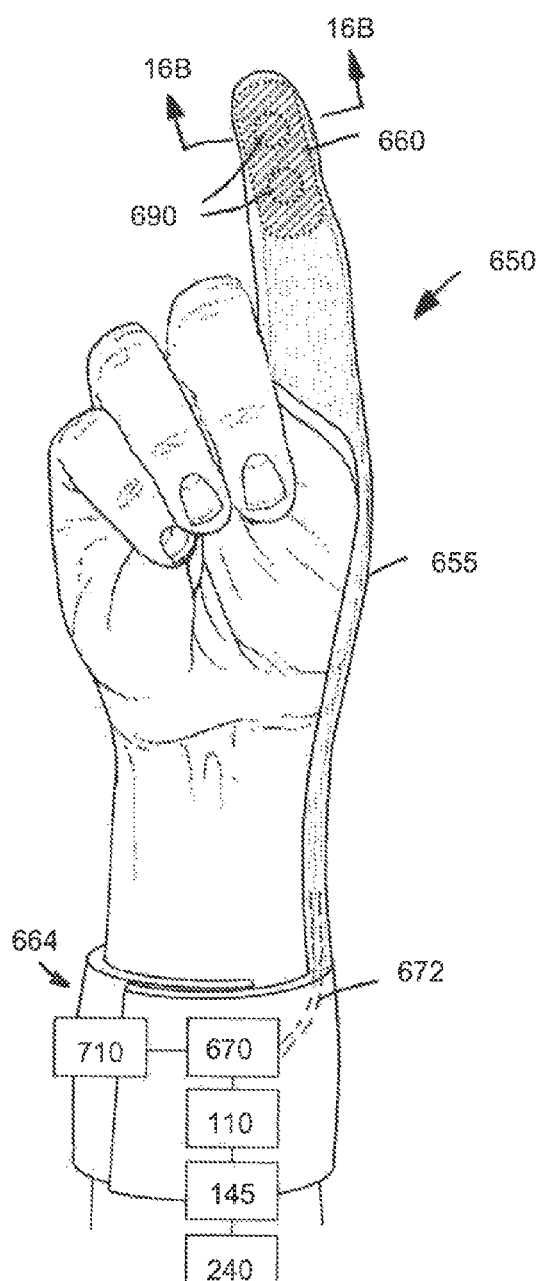
FIG. 16B
FIG. 16C
FIG. 16A

WEARABLE SENSING AND ACTUATOR SYSTEMS, AND METHODS OF USE

CROSS-REFERENCE TO RELATED APPLICATIONS

This application is a non-provisional of U.S. Provisional Application 62/095,740 filed on Dec. 22, 2014, the entirety of which is incorporated by reference.

FIELD OF THE INVENTION

This invention relates to wearable sensors and cybernetic systems that allow at least two individuals to interact and control operations of electronic, mechanical, robotic, or biomedical systems, and methods of use in gynecology, female sexual response and female sexual well-being.

BACKGROUND OF THE INVENTION

The field of wearable sensors is growing rapidly, with commercial products available for monitoring vital signs such as body temperature, heart rate, and respiration. In a recent report, Lux Research forecast that a new generation of sensors, called PFOE sensors (printed, flexible, organic electronic sensors) are destined for a future in which millions or billions of wirelessly-connected devices will form the much-discussed "internet of things", a large part of which may be wearable devices, including new medical and athletic wearable devices.

This invention relates to the field of systems using wearable sensors, and further includes wearable actuators, wearable control systems and wireless systems for communication between users wearing such systems. In a particular variation, this invention relates to wearable systems with sensors, actuators and control systems adapted for use in medical fields and the field of female sexual response and well-being.

In recent years, there has been an increased focus on women's health relating to sexuality and sexual response. On one track, physicians, researchers and pharmacologists have led a movement toward establishing female sexual dysfunction (FSD) as a new category of disease. In a well known 1999 JAMA study, the authors reported that 43% of surveyed American women experienced sexual dysfunction (*Journal of the American Medical Association*, Feb. 10, 1999). In this study, women were considered to have sexual dysfunction if they reported any of the following: lack of sexual desire, difficulty in becoming aroused, inability to achieve orgasm, anxiety about sexual performance, or failure to derive pleasure from sex. Further, the drug industry has attempted to draw parallels between male and female sexual dysfunction, following the success of Viagra (sildenafil) in treating male dysfunction. The success of sildenafil has made women's sexuality a high-profile research target.

On another track, women on their own have found means for addressing the issue of dissatisfaction is their sex life, and it is unlikely that they consider such dissatisfaction to be a disease state. In 2000, critics of categorizing female sexual dysfunction as a disease state were supported by the results of a preliminary study by the Kinsey Institute. The Kinsey data indicated that women considered that their emotional health and personal relationship factors were the most important factors in sexual well-being, rather than a quantitative metric such as achieving orgasm. In the Kinsey survey, women ranked general well-being at the top as a requirement, followed by emotional reactions during sexual activity, the attractiveness of her partner, physical responses during sexual activity, frequency of sexual activity with her partner, and her partner's sensitivity.

It seems likely the incidence of female sexual dysfunction has been exaggerated by parties other than the women themselves. However, there certainly is a lack of sexual well-being that is real for millions of women. In general, in women, sexual response is much more qualitative than in men and relates to desire, arousal, and gratification which cannot be easily observed or measured.

Women are taking active measures to enhance satisfaction in their sex life, and it appears that stimulus devices are popular and effective. In the 2005 Durex Global Sex Well-Being Survey it was reported that 43% of US respondents own a vibrator-type stimulus device. Similarly, a 2009 Indiana University study published in the Journal of Sexual Medicine found that 53 percent of all U.S. women have used a vibrator device.

Thus, it seems clear that stimulus devices may play a significant role in woman's sexual well-being. Such well-being is the result of a mind/body collaboration, that is, typically involving two minds and two bodies. What is needed are stimulus systems that are adapted for enhancing sexual response in women, while at the same time providing avenues for improving the personal relationship with her partner. More particularly, what is needed are new forms of stimulus systems that are enabled by discrete wearable sensors and actuators. Further, what is needed are cybernetic stimulus systems that will improve communications between a female and her partner while at the same time providing for optimal stimulus in intimate moments. Further, what is needed are cybernetic stimulus systems with data memory capabilities that are adapted to train or remind the partners of optimal stimulus inputs, or directly provide such inputs from algorithms that access the stored data.

The details of several variations of the invention are set forth in the accompanying drawings and the description below. Other features and advantages of the invention will be apparent from the description and drawings, and from the claims.

BRIEF DESCRIPTION OF THE DRAWINGS

FIG. 12A is a first component of another variation of a stimulus system that uses fluidic actuation with the component of FIG. 12A consisting of a non-disposable glove-like body that carries a drive unit or motor and sensors operated by finger movement.

FIG. 12B is a second component of the stimulus system of FIG. 12A with the component of FIG. 12B consisting of a disposable glove-like body that carries the fluidic actuator that is detachably coupled to the body of FIG. 12A.

FIG. 16A is a schematic view of another variation of a stimulus system which includes a glove-like device that carries a suction source that communicates with ports in the actuator region to suction tissue against the actuator surface.

FIG. 16B is a sectional view of the actuator region with an undulating surface of the device of FIG. 16A taken along line 16B-16B.

FIG. 16C is a sectional view of another actuator region of the device of FIG. 16A similar to that of FIG. 16B.

DETAILED DESCRIPTION OF THE INVENTION

Figure 1:
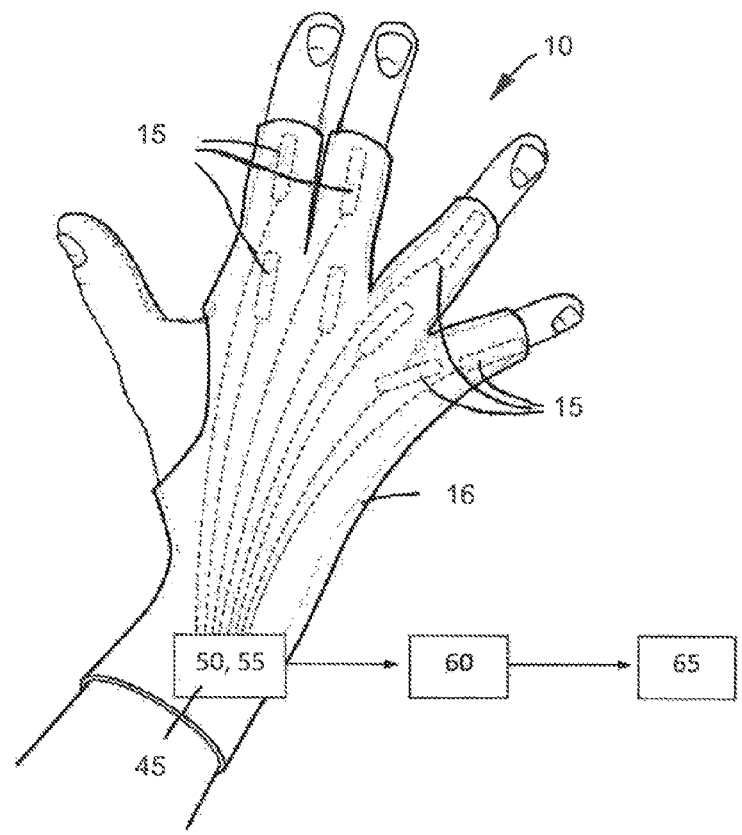
FIG. 1 is a schematic view of a glove-like device that carries a plurality of sensors positioned for stretchable actuation by a finger or knuckle joint, with each sensor coupled to a communication unit for sending signals to a control unit.
Figure 2:
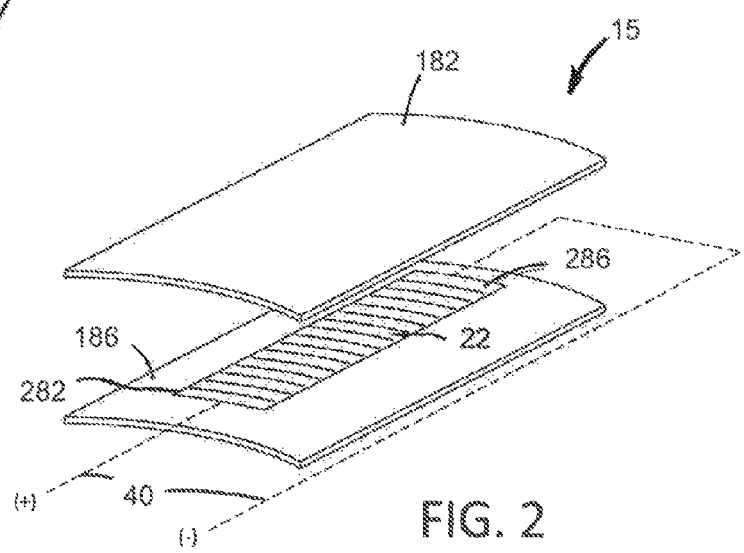
FIG. 2 is an enlarged exploded view of a stretch sensor that comprises a thin film conductive lyriform structure that can be embedded in an elastomer wall.

FIGS. 1-2 illustrate a wearable glove-like device 10 corresponding to the invention which carries a plurality of sensors 15 that can be affected or actuated by articulation of a joint in the user's hand, for example finger joints, knuckles or another joint. The wearable device 10 can have a form-fitting body 16 that is made of a thin woven stretch fabric or can be a molded elastomeric material depending on its application. In one variation, each sensor 15 can be a lyriform resistive sensor which is shown in FIG. 2 and which can be disposed between first and second layers 18a and 18b of an elastomer to form the sensor. The sensor can be carried in the form-fitting glove body 16 to be held close to a joint. The type of sensor shown in FIG. 2 comprises a very thin layer 22 of conductive material such as gold, platinum, copper or the like. The thin conductive layer 22 can be from about 10 nm to 50 microns in thickness. The thin conductive layer 22 is configured with a plurality of substantially parallel cuts or slits 25 which are intermediate the end portions 28a and 28b of the conductive layer 22 to which electrical leads 40 are coupled. As can be seen in FIGS. 1 and 2, the electrical leads 40 are connected to a battery 45 and communication unit 50. In operation, the battery 45 and a processor control chip 55 can control electrical current flow through the sensor 15, and stretching or flexing of the sensor will cause one of more of the slits to open and form a gap which will in turn greatly increase the resistance of the sensor, with corresponding signals registered by the processor chip 55 and communication unit 50. Thereafter, the communication unit 50 can send signals, for example, wirelessly to a control unit 60. The control unit 60 then can be operatively coupled to a target system 65, which be a radio, computer, dvd player, video game, toy, robot, exoskeleton, vehicle, aircraft, watercraft, remote tool, medical instrument, or other similar target system. The thin conductive layer 22 of the lyriform sensor can be from 1 mm to 20 mm in length, 1 mm to 10 mm in width and have from 1 to 1000 slits 25 therein. The elastomer layers that house the conductive layer can be silicone, urethane or a similar elastomeric material. The device body 10 can have from 1 to 20 or more sensors 15 close to a user's finger and/or thumb joints, knuckles, wrist, etc.

In one variation, the wearable device 10 can be coupled to a smartphone app, wherein the smartphone app is configured simply to provide a bluetooth link to a remote system to turn said system ON/OFF. For example, the wearable device 10 could be a user's driving gloves that carried a sensor of type described above with reference to FIGS. 2 and 3, and actuation of the sensor could turn an automobile radio or other auto accessory ON/OFF. In another variation, the sensor and its associated microcontroller can be configured to actuate the sensor sequentially to adjust the radio volume step-wise up and down, or change stations up and down, etc.

Figure 3:
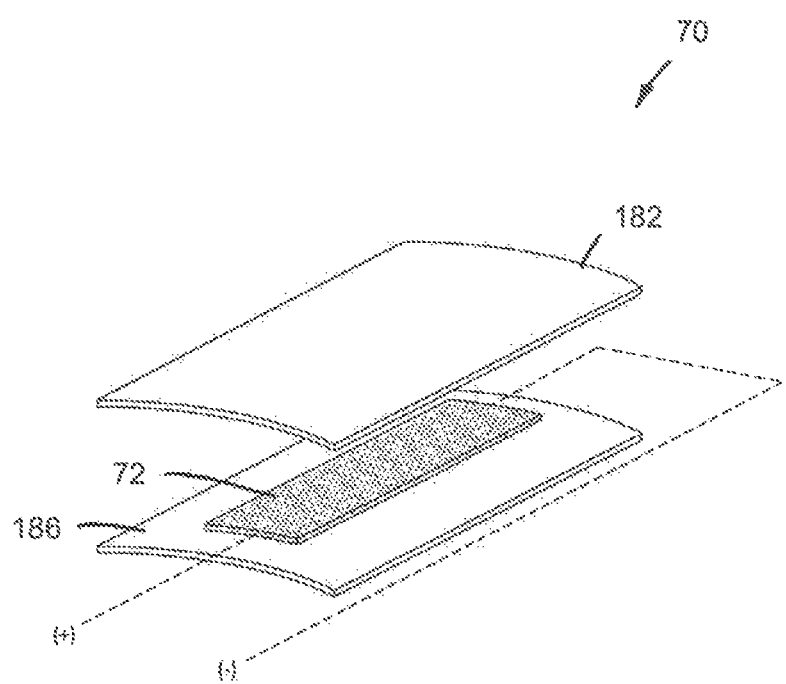
FIG. 3 is an exploded view of another stretch sensor that comprises a thin conductive polymer layer that can be embedded within an elastomer wall.

FIG. 3 shows another variation of sensor 70 which is similar that of FIG. 2 except the conductive layer 72 is a conductively doped polymer, such as a silicone doped with carbon or metallic particles. The conductive layer can be from 1 micron to 1 mm thick and also can optionally have lyriform slits therein (not shown). This sensor would operate similar to the sensor 15 of FIG. 2 described above. In another variation, the conductive layer of a metal or polymer can be a PFOE (printed, flexible, organic electronic) sensor with a printed pattern on an elastomer substrate and be adapted to increase resistance upon stretching.

Figures 4A, 4B:
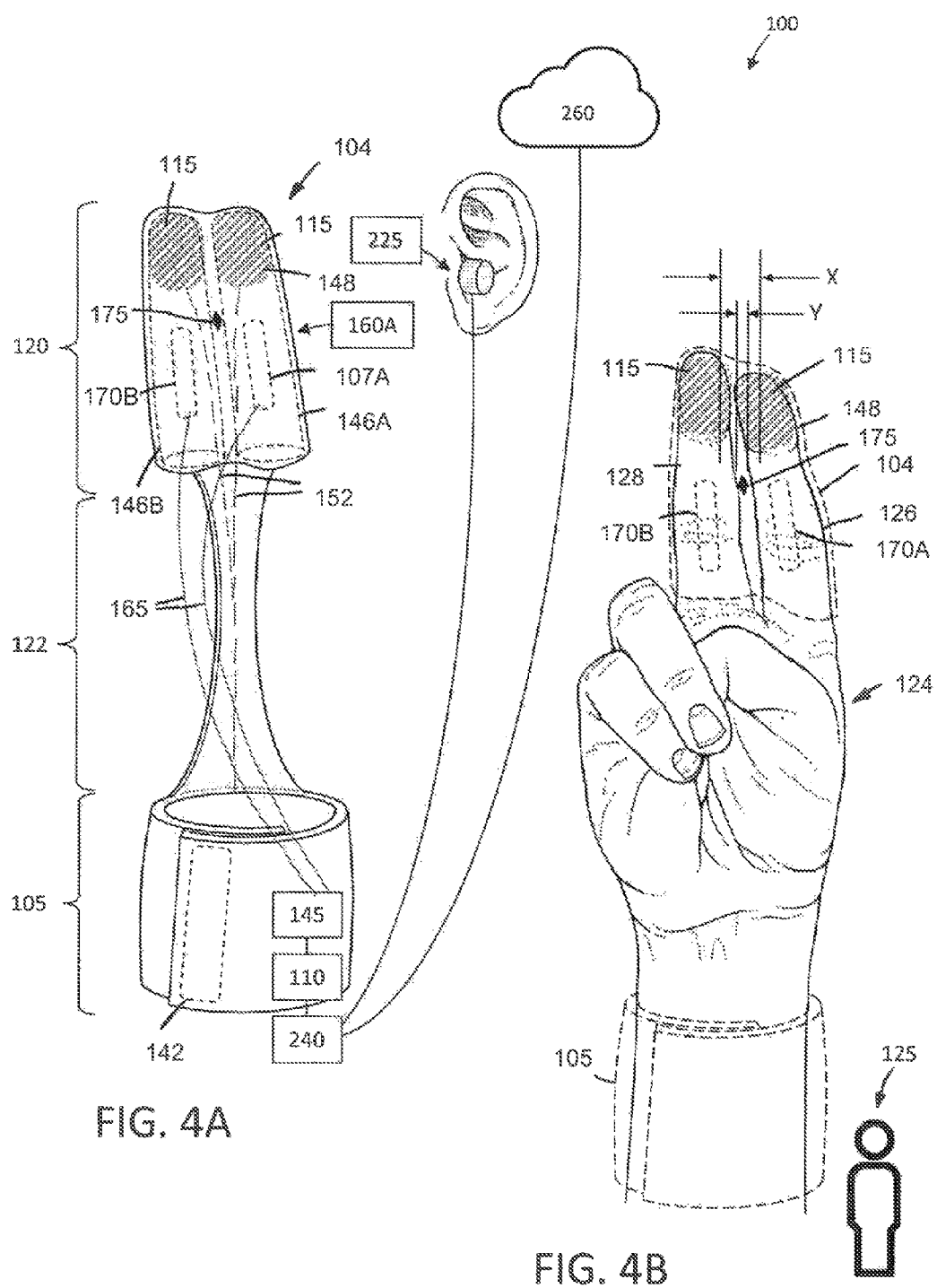
FIG. 4A is a schematic view of a stimulus system that uses fluid actuators corresponding to the invention with an elevational view of an actuatable device adapted for wearing on a human hand and controllable by finger movement.
FIG. 4B is a phantom view of the stimulus system of FIG. 4A disposed about a human wrist, hand and fingers.

Now turning to FIGS. 4 A-4B, 5 and 6, a variation of a stimulus system 100 using a dove-like device with sensors graphically represented. In FIGS. 4A-4B, the system 100 is adapted for applying stimulus to a female body and includes a form-fitting glove-like device body 104 that has a proximal body portion 105 that carries a drive unit 110 for actuating an actuatable region 115, a distal body portion 120 that carries at least one actuatable region 115 and a medial body portion 122 that operatively couples together the proximal and distal body portions 105 and 120. FIG. 4A schematically illustrates the device body 104 in perspective view and FIG. 4B shows the device body 104 in phantom view as worn by a human hand 124 and wrist or forearm of a first person 125. The system is configured for applying stimulus to targeted sites of a female body which can be any types of erogenous zone or tissue, herein at times referred to a sensory tissue. Such sensory tissue can be erogenous tissue of any type A-Z, for example, as identified at http://en.wikipedia.org/wiki/Erogenous_zone. The system 100 of FIGS. 4A, 5 and 6 is particularly adapted for stimulation of a female's Grafenberg spot, clitoris, among other sites with one objective being any type of orgasm in the female (e.g., clitoral, vaginal, squirting, etc.).

The system is also adapted for applying stimulus to sensory tissue that might not be commonly identified as an erogenous zone and may be individual-specific, with the objective of stimulus-induced 'frisson'. Frisson is a sensation akin to shivering, and is typically expressed as an overwhelming emotional response combined with piloerection or goosebumps. Frisson is a short duration pleasurable sensation, in which the skin of the lower back typically flexes, and shivers rise upward and inward from the shoulders and neck and may extend to the cheeks. The face may become flush and hair follicles experience piloerection. The sensation can occur in a series of waves moving up the person's back in rapid succession. The stimulus that is needed to produce a frisson is quite specific to the individual, but as will be understood from this disclosure, a female and her partner may experiment with the stimulus system and improve communication while experiencing the stimulus. A system adapted for frisson will have systems for audible stimulus as well as visual stimulus, and allows the partners to plan in advance what audible and visual stimulus may be optimal. Often, it would be expected that musical stimulus would enhance an episode and can induce or evoke frisson, which musical stimulus can utilize the earpieces 222 and 225 (see FIGS. 4A and 9) of the invention. Visual stimulus can be provided by computer screen, smartphone screen, or other light display device that may be in the background. The memory and control units of the system can harmonize and synchronize the tactile stimulus, audible stimulus, visual stimulus, and temperature stimulus, as will be described below.

Figure 5:
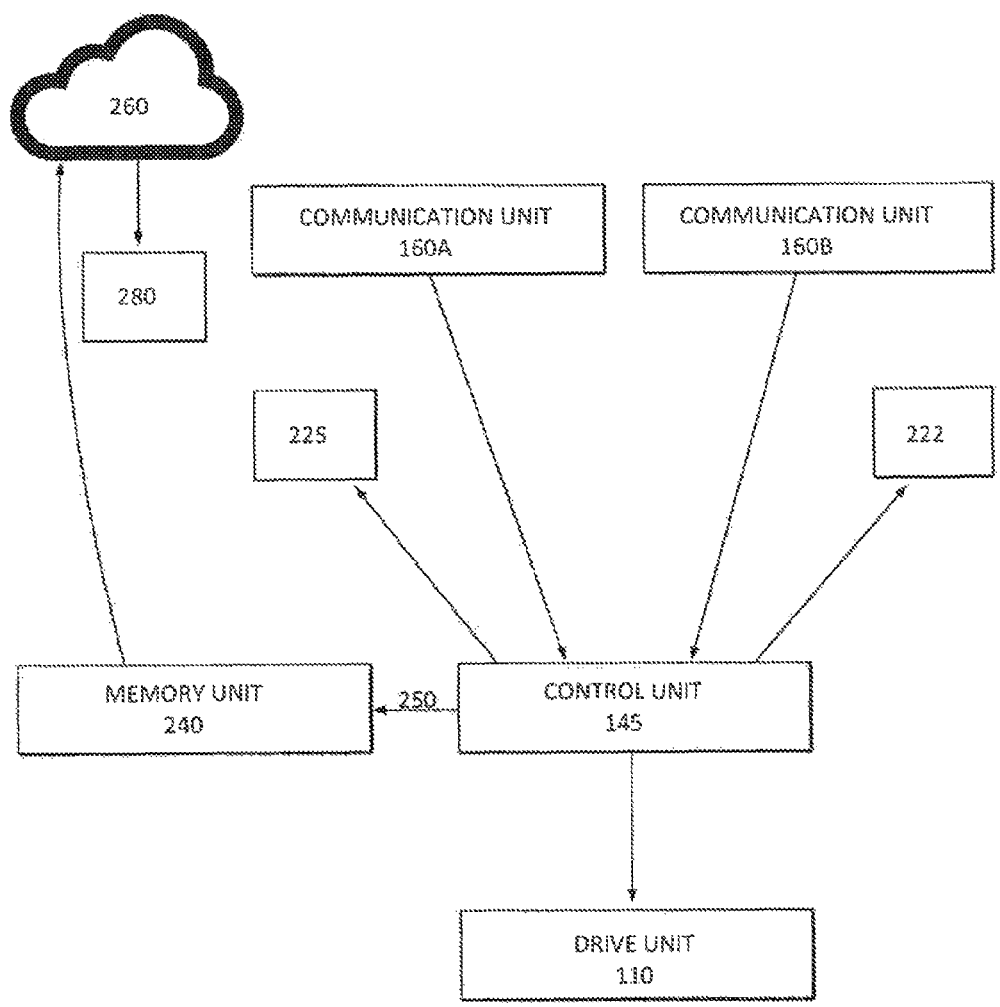
FIG. 5 is a block diagram of components of the stimulus system of FIG. 4A, including electrical components, wireless transmission components, controls units and memory units.
Figure 6:
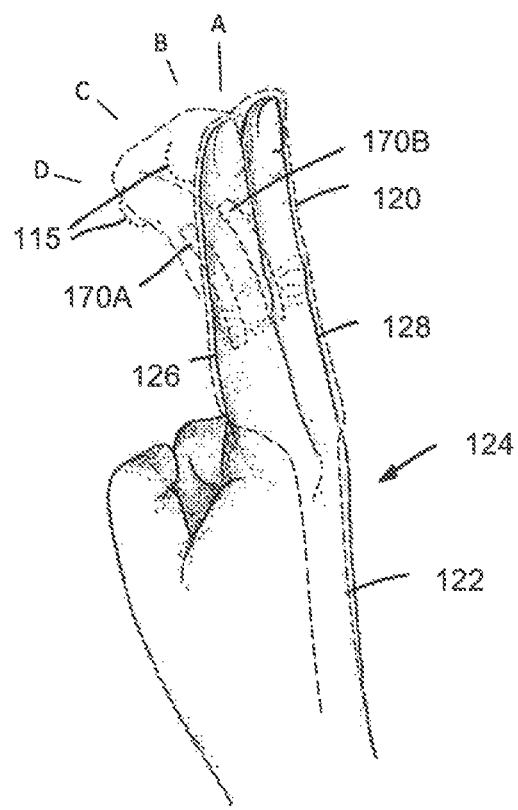
FIG. 6 is a view of human hand of FIG. 4B from a different angle showing finger actuation of stretch sensors of the stimulus system.

FIG. 5 is a block diagram of components of the stimulus system 100 of an exemplary variation of the invention described herein.

More in particular, the variation of FIGS. 4A-4B has a distal body portion 120 that is adapted to be carried by first (index) and second (middle) finger, 126 and 128, of first person 125 (or non-receiving partner as designated herein) who will use the distal body portion 120 to provide stimulus to a second person 140 (designated the receiving partner herein). In one variation, this distal body portion 120 can be fabricated of a flexible polymeric material such as silicone or a urethane. As will be described below, this distal body portion 120 carries sensors and electrical leads which can be embedded in a molded silicone or other similar flexible polymer.

In FIG. 4A, the medial portion 122 of the device body 104 also can be formed or molded of a flexible polymer and typically can be molded together with the distal body portion 120. The proximal body portion 105 is worn on the user's wrist and/or forearm and can have any type of wrap-around attachment mechanism, such as a fabric or polymeric hook and loop (e.g., Velcro) attachment 142. This body portion 105 can be fabricated of any suitable materials such as a stretchable woven material, molded or sheet silicone, etc. As will be described below, the proximal body portion 105 carries a drive source 110 and (optionally) a control unit 145 together with other electrical components which can be disposed in an interior chamber of a silicone (or other polymer) housing of the body portion 105.

Referring to FIGS. 4A-4B, it can be seen that the distal body portion 120 is dimensioned to fit over at least one user finger, and in this variation has first and second passageways 146a and 146b to receive two user fingers. The passageways 146a and 146b can have a closed end or be open-ended, and the device body around each finger can be closely coupled to on another or separated.

As can be seen in FIG. 4A, the distal body portion 120 carries at least one actuatable region 115, and in this variation has two independent actuatable regions, with each such actuatable region 115 proximate the location of the user's fingertips in each passageway 146a and 146b. By the term 'acutatable region', it is meant that a deformable or flexible surface 148 of the body 120 can be deflected, bulged or otherwise be pulsed outward from the body surface 148 in rapid intervals to thereby apply stimulating forces to targeted sensory tissue. In one variation shown in FIGS. 1 and 4A-4B, the actuatable region 115 is a fluidic actuator and can comprise a fluid-tight interior chamber 150 that communicates through flow channel(s) 152 with the drive source 110, which can be any suitable pump mechanism. This variation can be either pneumatic or hydraulic (i.e., gas or liquid actuated) with pump mechanisms described further below.

In the variation of FIGS. 4A-4B, the actuatable region 115 can have a surface dimension ranging from 5 $mm^2$ to 20 $mm^2$. In a high amplitude or high stimulus variation, the actuated region 115 can be fluid-actuated with an interior chamber 150 (see FIG. 11D) having a volume when expanded ranging from about 0.5 cc to 2 cc's or more. Of particular interest, the use of fluidic actuators allows for low or high amplitude pulses or displacement of the surface of body 148 and the control unit 145 allows for many variations in timing of pulse intervals as graphically represented in FIGS. 7A-7B, further described below. In this variation, the amplitude and actuation rate can be selected from a wide range, which is not possible with vibrating devices which typically use a coin type motor. When in use, the actuatable region 115 can deform, displace and pulse the elastomeric body surface 148 upwardly from about 0.5 mm to 2 mm, which is a much larger displacement than can be provided by conventional vibrator devices, such as eccentric motor vibration mechanisms. The wall of the body in which the actuator region 115 is carried can be very thin, for example less that 2 mm, less than 1 mm and less than 0.5 mm in thickness when the interior chamber 150 is not actuated. The control unit 145 can actuate the actuatable region 115 at rates ranging from 1 Hz to 50 Hz or more. In general, the fluidic actuator can operate at a lower pulse frequency than conventional eccentric motor vibrator mechanisms or other actuator mechanisms.

Of particular interest, a variation of the system as shown in FIGS. 4A, 4B, 5 and 6 includes a user-actuated communication unit 160A that sends signals indicated at 165 to the control unit 145 to operate the device. The system 100 includes intuitive finger-actuated means for controlling device operation, which includes turning the device ON/OFF, and controlling other selected operational parameters, which typically includes the amplitude of displacement of the actuatable region 115 and pulse rate (frequency) or sequence of intervals of displacement and relaxation of the actuatable region 115 (see FIG. 7A). In more complex variations, other operational parameters may be modulated which include the intensity or speed of the expansion phase of the actuatable region, the speed of the relaxation phase, including acceleration and deceleration rates in these phases. The time interval of the expanded or amplified state and the relaxed state also can be controlled. In still other variations, the system may use conventional vibrating motor components to produce stimuli, and similar finger-actuated mechanisms may be used. The system may also use a combination of fluidic and vibratory elements, as will be described below.

In one variation shown in FIGS. 4A, 4B, 5 and 6, the user-actuated communication unit 160A includes at least one stretch sensor in the distal body portion 120, and in this variation has first and second sensors 170a and 170b that can send control signals 165 to control unit 145. Each sensor 170a and 170b is disposed proximate a passageway 146a and 146b and is adapted to respond to stretching or bending forces caused by the user bending his or her fingers. A sensor can be a resistive stretch sensor be of the type shown in FIGS. 2 and 3 such that when the sensor body is flexed, the resistance across the sensor increases. Other types of flex sensors are known such as the type used in a Nintendo Power Glove. Sensors are available from Robot Mesh, 11232 120th Ave. NE, Suite 201, Kirkland Wash. 98033 USA. In one embodiment, the sensors 170a and 170b provide different signals for different degrees of flexing or stretching, thus the sensors can signal the control unit 115 to increase an operating parameter, for example amplitude or pulse rate over a range, depending on the degree of flexing of a sensor. Thus in one variation, as the user increasingly bends his or her fingers, the control unit 115 will increase the pulse rate of the actuatable region 115. In FIG. 4A, low power electrical leads (not shown) extend from the sensors 170a and 170b to the control unit 145. It should be appreciated that any type of sensor may be used, such as a capacitance flex sensors as is known in the art.

In a variation shown in FIGS. 4A-4B, the user-actuated communication unit 160 also includes a pressure sensor 175 in the distal body portion 120 between the finger receiving passageways 146a and 146b. This sensor 175 is adapted to respond to compressing forces caused by the user squeezing or tightening the space between his or her fingers to thereby compress the sensor 175. In one embodiment, a thin film type of pressure sensor can be used and can provide different signals for different degrees of applied pressure to thereby signal the control unit to increase an operating parameter over a range, for example, an amplitude range for actuatable region 115. A type of resistive pressure sensor is available from Tekscan, Inc., 307 West First Street, South Boston, Mass. 02127 USA. In FIG. 1A, the low power electrical leads to pressure sensor 175 are indicated at 176. It should be appreciated that any type of pressure sensor 175 may be used, such as a capacitance pressure sensor. It can easily be understood that a stretch sensor could be used in place of the pressure sensor, wherein the user would move his or her fingers apart to actuate the sensor.

Figure 7A:
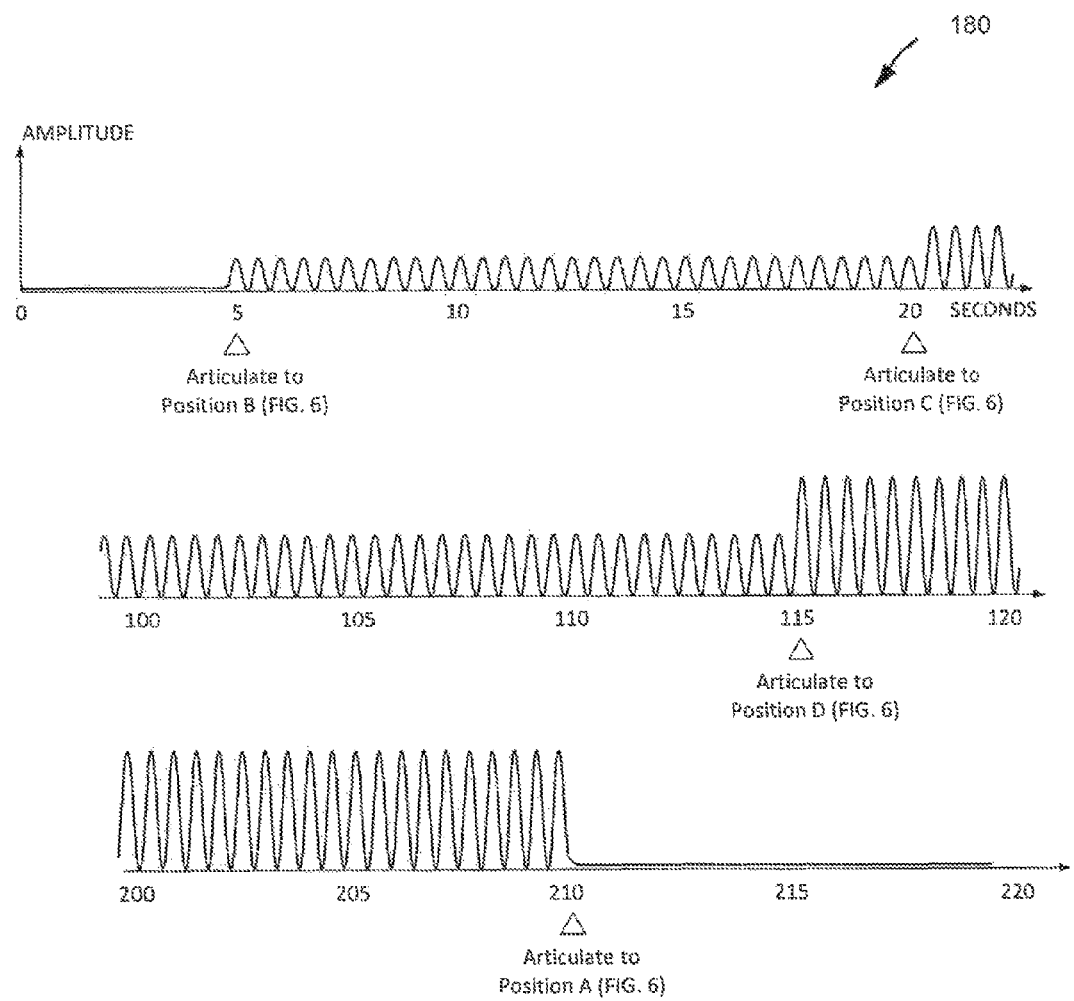
FIG. 7A is a chart showing a method of the invention relating to controlling the amplitude of pulses of an actuatable region of the device of FIG. 4A over a time interval or episode.

Referring to FIGS. 6 and 7A, aspects of the invention can be graphically illustrated. FIG. 6 represents the user's fingers articulating the device's distal body portion 120 between several positions. In a variation, the system 100 also uses the sensors 170a and 170b as an ON/OFF switch and the system is not actuated when the sensors are in the straight or repose position A of FIG. 6. The system is switched ON when the sensors are flexed a selected degree, such as a selected degree in the range of 5° to 20°, represented as angle B in FIG. 6 which corresponds to the '5 second' mark in FIG. 4A when the system is actuated. Thereafter, further flexing of the sensors 170a-170b in FIG. 6 to exemplary angles C and D sends control signals which indicate resistance, for example, and the control unit 145 increases amplitude at the corresponding '20 second' mark and '115 second' mark of a stimulus episode 180 as depicted FIG. 7A. The control unit 145 compares the control signal 165 from the sensors to a look-up table of values from which a corresponding power level to operate the drive unit 115 is selected, which in turn adjusts the amplitude of the actuatable region 115 as represented in FIG. 7A. In one variation, the person 125 wearing the device body 120 can simply articulate his or her finger and maintain the finger in a stable position and the drive unit 115 will actuate the actuatable region 115 at the predetermined amplitude and pulse rate. In other words, the non-receiving partner 125 can remain passive and the stimulation forces will be applied to the targeted site of the receiving partner. In FIG. 7A, at the '210 second' mark, the user 125 straightens his or her fingers to the angle indicated at position A in FIG. 6 and the actuation is turned off. FIG. 7A simply depicts graphically hypothetical amplitudes and pulse rates of stimulus over an episode 180 or time period of stimulation, wherein a real system can have more of a continuously variable amplitude based on the continuous flexing back and forth of sensors 170a-170b. In this variation, the two sensors are redundant.

Figure 7B:
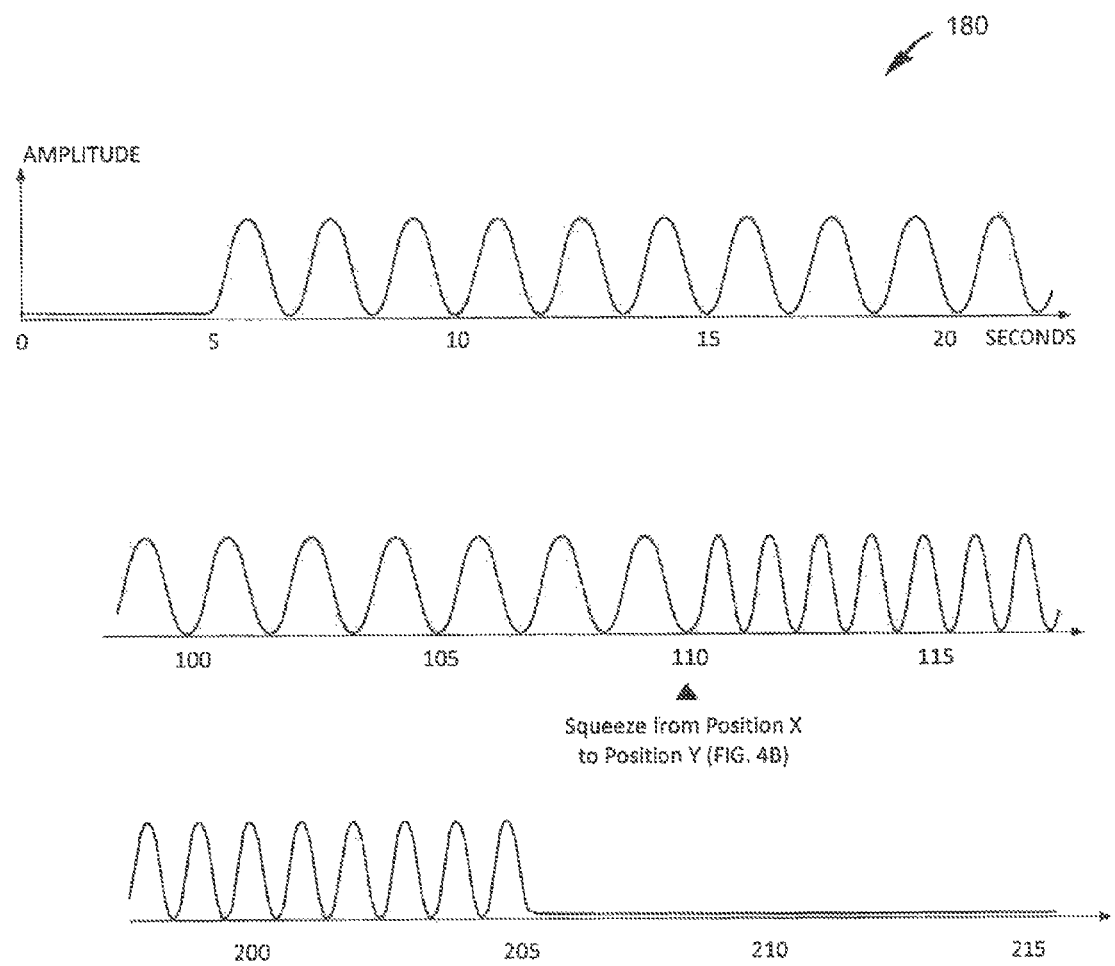
FIG. 7B is a chart showing another method relating to controlling the frequency of pulses of an actuatable region of the device of FIG. 4A over an episode or session.

FIG. 7A shows the system being operated at about 2 Hz, but it should be appreciated that any baseline frequency is possible that commences upon system actuation. After understanding FIG. 7A, it can be understood that the user 125 can contemporaneously actuate the pressure sensor 175 between the finger receiving passageways 146a and 146b (see FIG. 4A) to alter pulse frequency. FIG. 7B shows an example of user-actuated modulation of frequency wherein compression of sensor 175 increases pulse frequency. For simplicity, FIG. 4B indicates the compression of sensor 175 (from position X to Y) which corresponds to the change in frequency shown in FIG. 7B at the '110 second' mark. It should be appreciated that frequency can vary over a wide range in response to a range of compression levels of sensor 175.

From FIGS. 4A, 4B, 6, 7A and 7B, it can be understood that the system can vary an operating parameter by a very intuitive movement which is the simple flexing a finger or two fingers 126 and 128. At the same time, the fingers of the non-receiving partner 125 actually carry the actuatable regions 115 of the stimulus device—and all the while this partner 125 contemporaneously may be performing an independent digital stimulatory action at the targeted site of the receiving partner 140. In one variation, the increased flexing of a finger at the targeted site will be in the direction of increased actuator intensity at the site, which is logical and matches what the user might do in the absence of the device. Thus, in general, the invention can be considered to provide a biorobotic assist device that can simply apply the stimulus, or in another alternative can amplify, augment or otherwise modulate the stimulatory forces that a partner 125 wearing the device might provide to the receiving partner 140.

Figure 8:
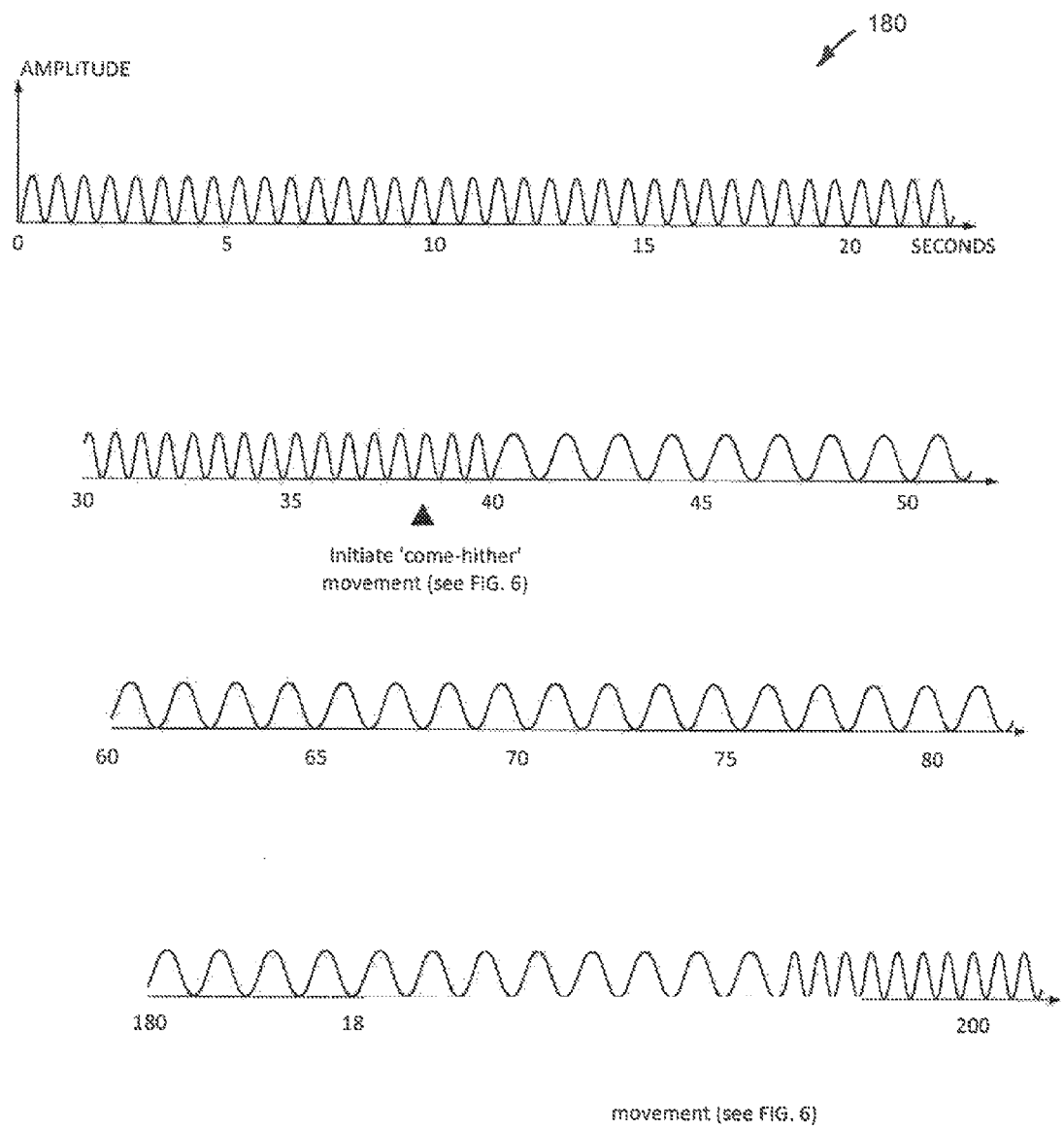
FIG. 8 is a chart showing another method relating to controlling the amplitude and frequency of pulses of an actuatable region of the device of FIG. 4A over a time interval.

FIG. 8 indicates another adaptive aspect of the invention wherein the stimulus system 100 accommodates active movements of the user 125, for example, the 'come-hither' movements of fingers by the non-receiving partner 125 during use of the stimulation system. For example, consider that the user 125 articulates his or her fingers back and forth generally as indicated FIG. 6, which shall be called come-hither movements herein. Such movements send signals from the sensors and communication unit 160A to the control unit 145. In one variation, the signals are processed by a control algorithm that monitors such a back and forth (come-hither) articulation of the fingers. If the algorithm detects rapid come-hither movements performed a predetermined number of times in short interval, for example 2 to 10 articulations in 1 to 5 seconds, then the algorithm will recognize that the non-receiving partner 125 seeks to actively use his or her fingers to provide stimulus together with the actuator stimulus, and thereafter the control unit 145 will adjust its control of the drive unit 110 to harmonize or synchronize the actuation of the actuator region 115 with the user's (i.e., non-receiving partner 125) digital movements. In this aspect, the control unit 145 can modulate the pulse rate (frequency) to match the non-receiving partner's rate of finger articulation, or in another algorithm provide a pulse rate that is a multiple of the rate of finger movement. In another example, the control unit 145 can modulate the amplitude in addition to frequency, for example, to provide that a pulse will reach its peak at each moment that the user's fingers are most articulated (i.e., position D in FIG. 6). In another variation, the amplitude of the actuation of the actuatable region 115 can be reduced a selected amount to harmonize with the user's digital articulation. In other words, the combination the partner's come-hither finger movements and the pulse amplitude may provide too great a stimulatory force on the target tissue, and this the control unit 145 modulates the intensity to allow the non-receiving partner 125 to be a more active participant. The control unit 145 can further provide an algorithm for detecting, when the non-receiving, partner stops 125 performing the come-hither finger movement, and thereafter the control unit 115 can take over control of the drive unit 110 to provide stimulus again based on the degree of sensor actuation for both amplitude and pulse rate. The algorithm can further provide a 'smoothing' code to insure there is a non-abrupt move from the 'modulated' operating parameters to the new operating parameters. Thus, algorithms on the control unit can insure that frequency and amplitude of stimulus are not in any way canceling the digital movements of the user, and instead are harmonized with the user's movements. This aspect of the invention will differentiate the experience for both partners from commercially available vibrator-type devices which are simply 'on/off' or a 'higher/lower' speed.

Figure 9:
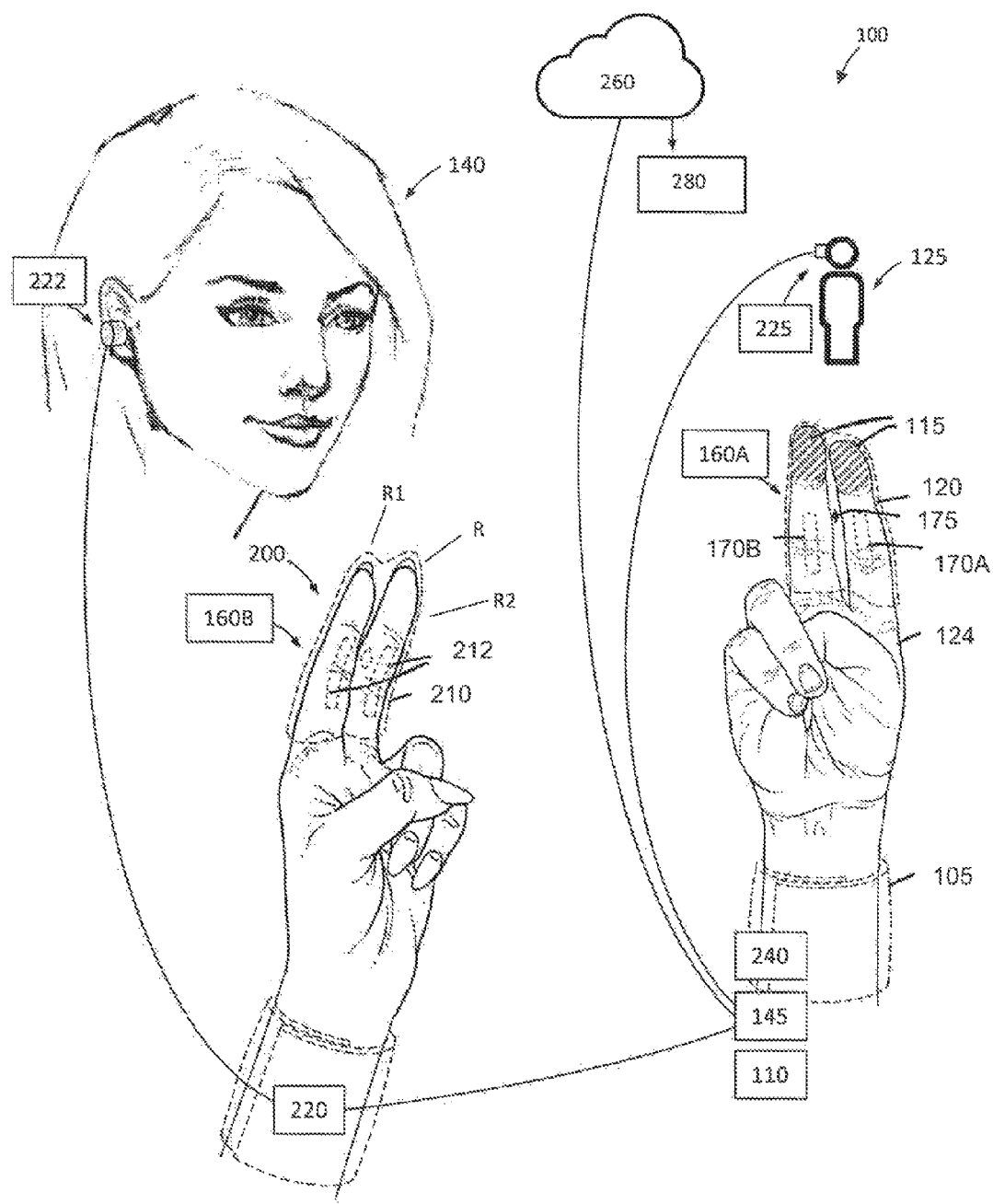
FIG. 9 is a schematic view of a stimulus system as in FIG. 4A further including a second actuatable device adapted for wearing on a second person's hand.
Figure 10:
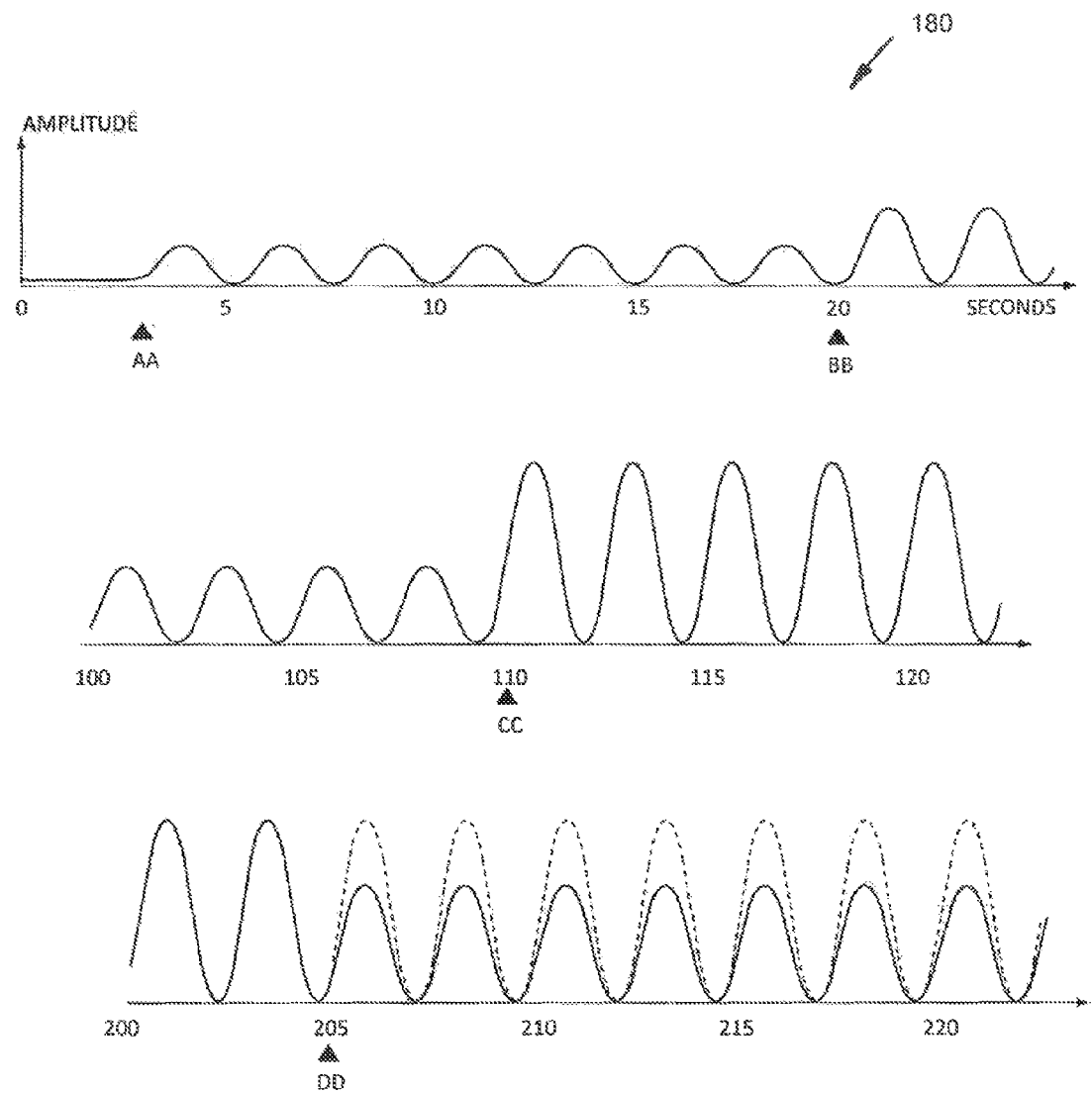
FIG. 10 is a chart showing another method of the invention relating to two partner's interactively controlling the amplitude of pulses of an actuatable region of the device of FIG. 4A over a time interval.

FIGS. 9 and 10 illustrate another interactive and adaptive aspect of the invention wherein the system 100 provides for a subtle, non-verbal interaction between the receiving partner 140 and the non-receiving partner 125 during a stimulation episode 180. In FIG. 9, it can be seen that the female or receiving partner 140 wears a device 200 having a device body 210 on her hand, which in one embodiment can be a body that can fit over one or more fingers. In the variation of FIG. 9, the receiving party's device body 210 resembles the distal body portion 120 of the non-receiving partner's wearable device. The device body 210 of FIG. 9 is adapted for manipulation by the receiving party 140 to 'fine tune' or modulate the stimulatory forces applied to her targeted sensory tissue during a stimulus episode 180 in which the intensity is initiated by her partner (i.e., the non-receiving partner 125). In one variation, the device body 210 has at least one stretch or flex sensor 212 that is a part of a second communication unit 160B and transmitter 220 that is adapted to send signals to the control unit 145. As in the non-receiving partner's device 120 (see FIG. 4A), the sensor 212 can send a plurality of signals via a transmitter 220 (in this case wirelessly, e.g., in Bluetooth) dependent on the degree of articulation of her fingers. In the variation of FIG. 9, the device body 210 carries two sensors, but they can be considered to be redundant and signals therefrom are conformed by the second communication unit 160B and control unit 145 into a single signal 215 which is sent to the drive unit 110.

The receiving partner 140, or the partners together, can select between different modes of 'interaction' to operate the device 210 and thereby interact with the stimulus system 100. More particularly, the receiving partner can select a manner in which her device body 210 can be manipulated to modulate the intensity of stimulus that has been initiated by the non-receiving partner 125. The mechanics of mode selection is further described below. In one interaction mode, for example herein called a cooperative or 'fine-tuning' mode, the receiving partner's purposeful flexing of the sensor 212 (see FIG. 9) signals the controller 145 to augment or reduce the intensity at which other (non-receiving) partner 125 is operating the device 120 and actuator region 115. In this embodiment, the sensor 212 can have an intermediate 'rest' position or 'no-adjust' position indicated at R which signals the control unit 145 to make no changes in the on-going operating intensity parameters. The sensor 212 in a less articulated or straightened position R1 can send signals to progressively reduce the on-going (and potentially changing) intensity that is set or being adjusted by the non-receiving partner 125. The term intensity as used herein means amplitude, frequency, or the combination of amplitude and frequency. If the receiving partner 140 moves her fingers to the more articulated position R2, the sensor 212 sends signals 215 that will progressively increase the intensity of the stimulatory forces. This mode of operation then makes both partners' inputs contemporaneously interact to ultimately control the drive unit 110, with the receiving partner 'fine-tuning' the stimulatory forces which only the receiving party 140 can optimize in an immediate and non-verbal manner. In an on-going stimulus episode 180, then both partners can continue to modulate inputs and the resulting stimulatory effects. This mode can continue until the receiving partner 140 returns the sensor 212 to its rest position R in FIG. 9.

FIG. 10 graphically depicts a hypothetical episode of interaction between the partners 125 and 140. In FIG. 10, the non-receiving partner 125 actuates the system at time BB which provides a certain amplitude and frequency of stimulus using the device body as described previously. That partner 125 then at time BB and at time CC increases the amplitude of stimulation. Then, at time DD, the receiving partner 140 actuates her device 210 from the rest position R to the R1 position (see FIG. 9) which lowers and fine-tunes the amplitude to provide the desired level of stimulus. As can be seen in FIGS. 4A, 9 and 10, the partners wear wireless (e.g., Bluetooth) earpieces 222 and 225, which can serve the purpose of providing a subtle, non-verbal means of informing the partners of each others actuation of system components. In this case, the receiving partner's modulation of stimulus may be accompanied by a tone in earpiece 225 of her partner 125, which will be a cue that the receiving partner 140 wishes to fine-tune the stimulus. The tone, or sequence of intermittent tones, can be configured to indicate to the non-receiving partner 125 whether the actuation is being up- or down-modulated by the receiving partner 140. Additional aspects or this 'fine-tuning' interaction mode will be described below.

In a second mode of interaction, the receiving partner's articulation of the body 210 and sensor 212 will displace and replace signals from the non-receiving partner's first communication unit 160A which can be termed a 'replacement' mode. In selecting this mode, the receiving partner 140 in effect seeks to temporarily control the intensity of the stimulatory forces applied to the target site. The receiving party can then adjust intensity by variably flexing the sensor 212. Again, this replacement mode can continue until the receiving partner 140 returns the sensor 212 to its rest position R in FIG. 9.

In a third mode of interaction, the receiving partner's articulation of body 210 and sensor 212 will interrupt and replace signals from the non-receiving partner's first communication unit 160A for a time interval, for example from 2 seconds to 20 seconds or more which can be termed an 'interruption' mode. In selecting this mode, the receiving partner 140 wishes to influence the stimulatory forces, but also may wish to receive her partner's spontaneous or unpredictable modulation of stimulatory forces. This mode can continue until the end of a pre-selected time interval, or the mode can end when the receiving partner returns the sensor 212 to its rest position R.

The non-receiving partner's wearable device 210 can utilize one of several types of mode-selection mechanisms, and in one variation uses the pressure sensor 222 to signal the control unit as to which mode is selected. For example, the pressure sensor 222 can be pressed twice in a sequence comparable to a 'double-click' of a mouse to cycle through the options of the three modes. In effect, a selected sequence of manipulations can be adapted to select the interaction mode desired by the receiving partner 140. A similar sensor arrangement can be provided on the receiving partners device body 210.

In another aspect of the invention, referring to FIGS. 4A, 5 and 9, the system also includes a memory unit 240 which can record the data that reflects the modulating operating parameters that were utilized over a stimulus episode or session. In one variation, the data 250 (FIG. 5) can be sent wirelessly from the control unit's processors and memory to a base memory unit 240 for storage and/or to a cloud-based memory unit indicated at 260 in FIGS. 5 and 9.

In one variation, the memory units 240 of 260 store data that reflect each episode 180, which can be viewed in a display (i.e., phone, tablet or computer) in condensed graphic form much as depicted in FIGS. 7A, 7B, 8 and 10 to show amplitude and frequency of stimulus during an episode. In particular, the data in a memory unit 240 or 260 can be displayed to highlight portions of an episode 180 in which the receiving party 140 modulates the input and stimulus initiated by the non-receiving party 125. This 'modulating' data can then be instructional to the non-receiving party 140 for use in a future stimulus episode between the receiving and non-receiving parties 140 and 125. This data can is useful in an aspect of the invention which is to enhance communication between the partners and thus which can contribute to enhanced female satisfaction with her partner.

In another variation, the control unit 145 and memory units 240, 260 (FIGS. 5 and 9) are designed to provide feedback to the users, based on having algorithms that analyze one or more previous stimulus episodes. In one example, the control unit 145 can compare a number of previous episodes and determine if there is any common characteristics under which the receiving partner 140 intervenes to modulate the non-receiving partner's 'leading-to' stimulus inputs that led up to her intervention. Such 'leading-to' inputs can relate to stimulus intensity, interval of time following start of the episode, etc. If the control unit 145 and its algorithms find comparable interventions and stimulus modulations by the receiving partner 140, then the control unit 145 in real time can 'look' for similar 'leading-to' inputs and if such inputs are identified, then the control unit can signal the non-receiving partner that he or she is delivering such 'leading-to' stimulus, which signal can be a tone in the earpiece 225. The control unit 145 could signal the partner 140 by another means, such as a vibrator in the device, electrode stimulation, etc., for a non-receiving partner 125 that might be inattentive, distracted, tired or otherwise asleep at the wheel. A tone signal in the earpiece 225 could also have tone features that indicate an up-modulation or down-modulation is needed to match the prior data of receiving party intervention. The control unit also can notify the receiving partner 140 of the 'leading to' inputs by her partner, which may usefully remind her of the previous episode, inform her that the system has discovered a commonality among the previous episodes, and/or allow intentional non-intervention to permit her partner to independently modulate inputs. The system 100 thus can provide a form of subtle intervention that can unobtrusively assist both partners in optimizing stimulus in an episode. In another variation, algorithms may be developed based on group data (see below) and will function as a form of artificial intelligence to suggest stimulus options to either or both of the partners during an episode. In another variation, the users can elect to have the artificial intelligence algorithms assume control of stimulus, it the system sees a pattern for which it has a calculated response, or a partner 125 who is remote from the receiving partner 140 could use remote access to control stimulus with the receiving partner wearing and positioning the device at the targeted sensory site.

Figure 11A:
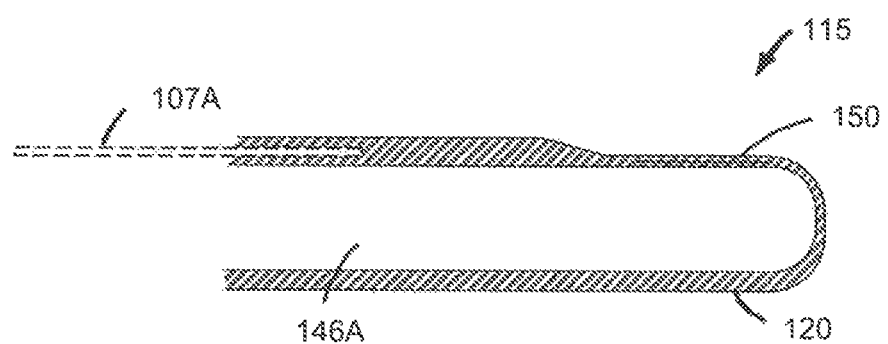
FIG. 11A is a sectional view of a fluidic actuator region of the device of FIG. 4A in a non-actuated position.
Figure 11B:
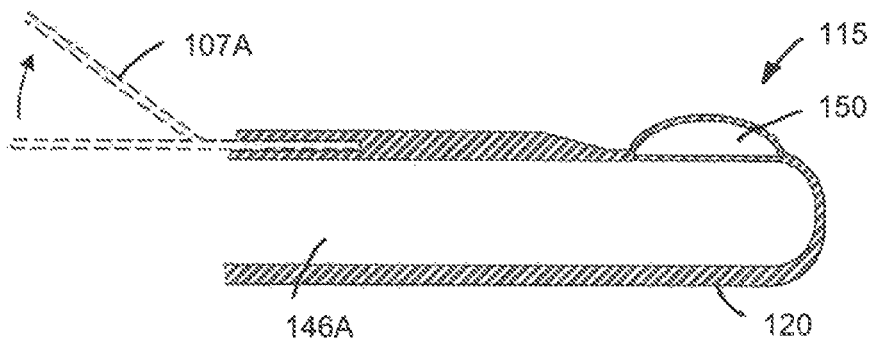
FIG. 11B is a sectional view of a fluidic actuator region of FIG. 11A in an actuated position.

FIGS. 11A-11B show schematic sectional views of the actuator region 115, and illustrates that the polymer material on either side of the actuator chamber 150 can be very thin, for example, from about 0.02 mm to 0.5 mm which can be as thin as a condom. This is unlike other vibrator devices which do not allow for intimate contact between partners. In this variation, when the actuator region 115 is non-actuated (FIG. 11A), the contact between the non-receiving partner's fingers and the tissue of the targeted site will be very close, practically as if the device did not exist. In another variation, the actuator region 115 itself or the area surrounding it can be perforated to allow further tactile sensing through the membrane. In the variation that has a perforated actuator region 115, the region would expand around each such perforation or aperture and amplitude would be lessened compared to an actuator region as shown in FIG. 11B.

In another variation, referring back to FIG. 5, a memory unit can make the data available to a central analytic processing (CAP) system 280 which can assemble and analyze data from a plurality of episodes of different receiving parties 140 (group data). For example, the manufacturer of the system or an independent analytics group associated with system manufacturer can provide an analytic system to which users can anonymously and voluntarily send episode data. Each user can have an ID number, and the data can be accompanied by user definition of the type or objective of the episode (e.g., type A-Z as referenced above) and other relevant data. The CAP system 280 then can process that data to compare different users' stimulus parameters and outcomes which can lead to potential new understandings of stimulus and response. Such data may be useful for medical and pharmacological research in fields relating to female response to stimulus as described herein where data is certainly lacking.

In general, a method of the invention for promoting well-being in a female comprises stimulating a first (female) person's target sensory tissue with a second person's digital movements to apply stimulus wherein the digital interface with the site includes a thin member worn by the second person and wherein the thin member includes a fluidic actuator. Further, the fluid actuator is actuated by, and actuation parameters are controlled by, the second person's digital movements. The method further comprises controlling an actuation parameter by signals from the first person and/or by signals from a control unit 145.

In a method corresponding to the invention, a first person wears a stimulus device and contacts a female's targeted site with the device wherein the first person sends first control signals to a control unit to select operating parameters of a drive mechanism of the device to apply a stimulus to the site and wherein the female in response to sensations from the stimulus sends second control signals to the control unit to adjust the operating parameters.

FIGS. 12A-12B illustrate another variation of stimulus system 400 that is similar to the previously described version except the system's functional parts are separable to provide re-useable and disposable components. In FIG. 12A, a non-disposable wearable body 402 is shown which can be glove-like that again has a proximal portion 405 that carries the drive source 110, control unit 145 and memory unit 240. The bulk of body 402 can be a woven material that is very thin and flexible similar to a woman's nylon stockings. The body 402 has a distal portion 420 that carries at least one sensor 425 that operates as described previously. Such a sensor 170 can be positioned proximate a finger or knuckle joint, or another hand joint, to be actuated by finger or hand motion. For example, the sensor 425 can be on the outside or inside of a finger joint and is shown on the outside of the finger joint. Although two sensors are shown, a single sensor positioned on one finger is possible. While FIG. 12A shows a glove-like body 402, another variation as in FIG. 13 can simply have a proximal body portion 405 as described above with electrical leads 418 coupled to an elastomeric portion that carries sensor 425 and is configured for fitting over a finger.

Referring to FIGS. 12A and 12B, it can be seen that the non-disposable wearable body 402 does not carry the actuatable region 115. Instead, FIG. 12B shows a disposable body 440 that is adapted for wearing over the sensor-carrying body 402 and is configured to carry the at least one actuatable region 115. The disposable body 440 has a proximal end 442 that has a connector 445 for coupling to the proximal body portion of the non-disposable body 402, for example coupling pneumatic flow channels 448a and 448b to the drive unit 110 or pump mechanism in the non-disposable body 402. In this embodiment, the disposable body 440 can be very thin, for example, 0.02 mm to 0.10 mm in thickness to allow for maximum sensitivity between the partners. In one variation, the connector 445 can couple a pneumatic line and channels 448a and 448b to an air pump. In another variation, the connector 445 can lock a sealed chamber or bladder (not shown) carried by the disposable body 440 into a receiving part of the non-disposable body 402. The pump mechanism in this variation is a motorized component that compresses and decompresses the chamber or bladder to actuate the actuatable region 115.

Referring to the variations described above, the pump systems can be of any type, for example an electromagnetic pump as known in the art and used in fluidic systems. Other types of micro- or miniature pumps can be used, such as piston pumps, diaphragm pumps, vane pumps, roller pumps, peristaltic pumps, screw pumps, impeller pumps and the like. Various micropumps and systems for use in fluidic systems are described in the following U.S. patents which are incorporated herein by reference: U.S. Pat. Nos. 8,616,227; 8,591,834; 8,590,573; 8,389,960; 8,343,442; 8,282,896; 8,206,593; 8,168,139; 8,157,434; 8,105,824; 8,104,514; 8,058,630; 8,007,746; 7,837,946; 7,695,683; 7,691,333; 7,666,361; 7,640,947; 7,476,363; 7,392,827; 7,368,163; 7,291,512; 7,118,910; 7,075,162; 7,005,493 and 6,953,058.

The proximal portions of the systems described above that are worn on the user's wrist carry a battery that may be replaceable or re-chargeable. In one variation, the battery can be an inductively re-chargeable battery as is known in the art.

In another variation, the device worn by the user can include one or more accelerometers which can send signals to the control unit and memory unit. Such accelerometer signals can detect and quantify the user's finger movements separate from the fluidic actuator's movements and such signals can be used in feedback to the user during use, for storage in the memory unit for future reference as to preferences, for providing, limits to system actuation, etc.

Figure 13:
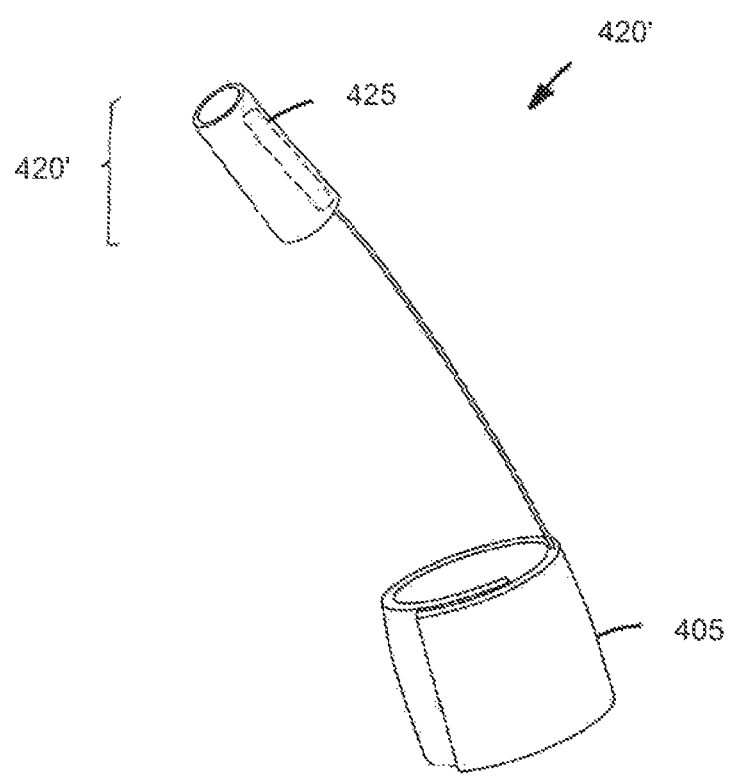
FIG. 13 is another variation of the first component of a stimulus system similar to that of FIG. 12A.

FIG. 13 illustrates a non-disposable wearable body 40T that is a variation of the first component of a stimulus system similar to that of FIG. 12A. In this variation, the body 40T has a reduced form factor with a single sensor 425 that is carried on a distal portion 420' adapted for fitting on a single human finger.

Figure 14:
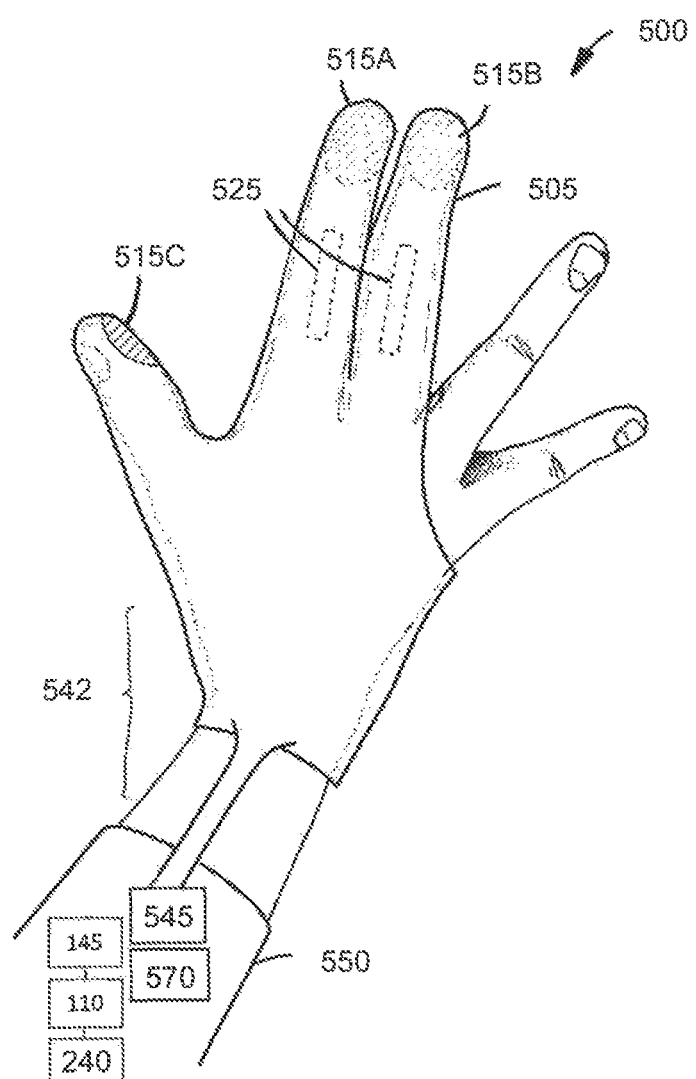
FIG. 14 is a view of another variation of a stimulus system which includes an entirely disposable glove-like stimulus device of the type illustrated in FIGS. 4A-4B or FIGS. 12A-12B that carries both sensors and actuatable regions.

FIG. 14 is a view of another variation of a stimulus system 500 which includes an entirely disposable glove-like stimulus device 505 similar to the types illustrated in FIG. 9 and FIGS. 12A-12B that includes actuatable regions 515a, 515b and 515c and at least one sensor 525 carried therein. The sensor 525 can be a lyriform sensor of the type shown in FIGS. 1-2. The actuatable region again can be fluidic chambers 105 (see FIG. 11B) within in a very thin elastomer wall as described previously. FIG. 14 shows that the proximal part 542 of the device 505 includes a connection portion 545 for coupling to a wearable body 550 carrying a drive unit 110, control unit 145 and memory unit 240 as described previously. In all other respects, the stimulus system 500 of FIG. 14 operates as described above with the variations of FIGS. 4A and 9. In one variation, the connection portion 545 comprises a resilient tubular member with a sealed interior chamber that communicates with the actuators fluidic chambers 150 (see FIG. 11B), and the drive unit 110 can be a roller that alternatively compresses and relaxes the resilient tube to drive the actuator regions 115a-115c. The sealed fluidic system can be filled with air or a liquid such as sterile water.

In one variation that is directed to stimulation and/or causing a frisson effect, the system can carry a liquid that can be cooled in the wearable body 550 by a cooling mechanism 570 which can be a Peltier element. In another variation, the fluidic system can provide for circulation to and from the actuator portions 540*a*-540*c* and a coolant fluid can be provided by a liquid gas cartridge or canister (e.g., a CO2 canister, argon canister or liquid nitrogen canister) that is detachably coupled to body 550 for a single use of limited use.

FIG. 14 is a view of another variation of a stimulus system 500 which includes an entirely disposable glove-like stimulus device 505 similar to the types illustrated in FIG. 9 and FIGS. 12A-12B that includes actuatable regions 515 *a*, 515 *b* and 515 *c* and at least one sensor 525 carried therein. The sensor 525 can be a lyriform sensor of the type shown in FIGS. 1-2. The actuatable region again can be fluidic chambers 150 (see FIG. 11B) within in a very thin elastomer wall as described previously. FIG. 14 shows that the proximal part 542 of the device 505 includes a connection portion 545 for coupling to a wearable body 550 carrying a drive unit 110, control unit 145 and memory unit 240 as described previously. In all other respects, the stimulus system 500 of FIG. 14 operates as described above with the variations of FIGS. 4A and 9. In one variation, the connection portion 545 comprises a resilient tubular member with a sealed interior chamber that communicates with the actuators fluidic chambers 150 (see FIG. 11 B), and the drive unit 110 can be a roller that alternatively compresses and relaxes the resilient tube to drive the actuator regions 115 *a*-115 *c*. The sealed fluidic system can be filled with air or a liquid such as sterile water.

In other variations, the wearable device carrying the drive unit, control unit and/or memory unit can be worn at least in part by a body portion selected from the group of a hand, wrist, arm, leg and torso. In other variations, sensor can be configured to respond to bending, stretching, compressing, shaking, swiping, touching or a combination thereof. For example, a device worn on a torso can be useful for a system that can be operatively and detachably connected to a condom that carries one or more fluidic actuators of the types described above (cf. FIGS. 12-12B).

In another variation, an actuatable region 115 of a stimulus device of the type shown in FIG. 4A or 12B can have an actuatable region 115 including apertures extending through and around the expandable fluidic chamber 150 (not shown).

In other variations, the actuatable region 115 can optionally consist of alternative actuator mechanisms, including at least one of an eccentric rotating mass vibration mechanism, a linear resonant actuator, a piezoelectric actuator and an electro-active polymer actuator. In another variation, the actuatable region 115 can be a fluidic chamber as described above overlying one of the just-described alternative actuators (not shown). In another variation, the actuatable region 115 can be an annular fluidic chamber with one of the just-described alternative actuators surrounded by the annular fluidic chamber (not shown).

A method of making a stimulus device, comprising providing first and second elastomeric layers and bonding together said first and said second elastomeric layers except for a flow channel and chamber to form a monolithic elastomeric structure as can be understood from FIGS. 12A-12B.

Another method of the invention can be understood from the description above and FIGS. 4A-4B and 9, the female or receiving partner could wear the glove-like device having the actuatable regions and position these regions in contact with her sensory tissue and then allow her partner to control the system operation remotely which may be useful for episodes in which the partners are in different locations.

In the system variations described above, there may be a default mode of harmonizing inputs from the users when the system is activated, with the stimulus parameters pre-selected for various degrees of actuating the sensor 170*a* and 170*b* as described with reference to FIGS. 2-6. In another variation, a smartphone, iPad or similar devices may be adapted to communicate with the control unit to change the operating mode, or to adjust default stimulus parameters. In general, a method of the invention comprises engaging targeted female sensory tissue with an actuatable device surface worn by a human hand, applying stimulus from the device surface to the targeted tissue and selecting operating parameters on a touchscreen of a wireless device communicating with a controller operatively connected to the actuatable device.

Figure 15:
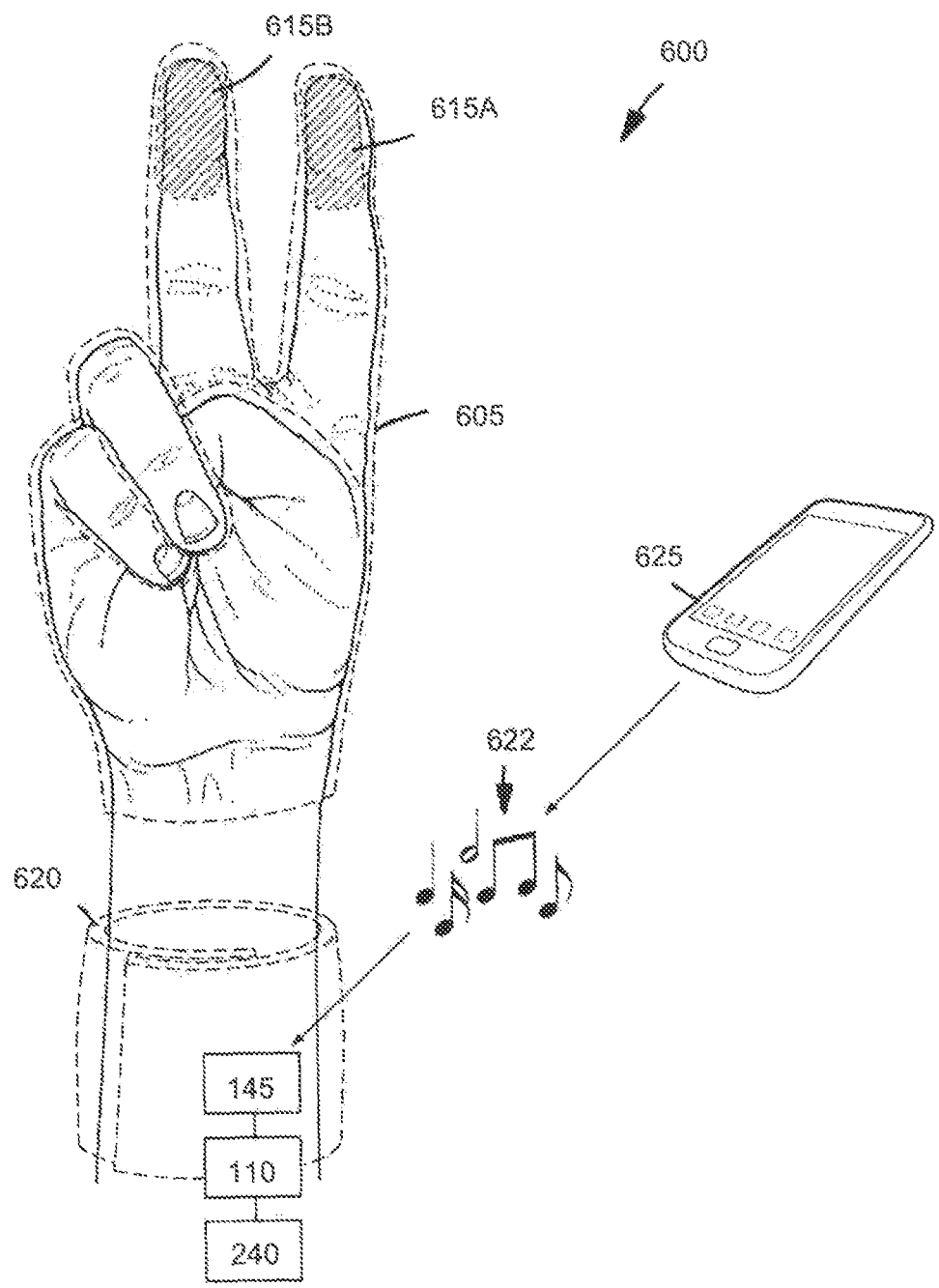
FIG. 15 is a schematic view of another variation of a stimulus system which includes a glove-like device of the type illustrated in FIGS. 4A-4B that has a control unit that is adapted to receive music signals and controller algorithms that can modulate applied stimulus in response to aspects of music.

FIG. 15 schematically depicts another variation of a stimulus system 600 which again includes a glove-like stimulus device 605 similar to the type illustrated in FIG. 9, with the device 605 having actuatable regions 615*a* and 615*b*. The actuatable regions again can be fluidic chambers 105 (see FIGS. 11A-11B) within in a very thin elastomer wall as described previously or can be an eccentric rotating mass vibration mechanism, a linear resonant actuator, a piezoelectric actuator or an electro-active polymer actuator. The proximal part 620 of the device 605 again carries, or is coupled to, a drive unit 110 for driving the actuator regions 615*a* and 615*b*, a control unit 145 and a memory unit 240 as described above. In this variation, the control unit 145 is adapted to receive signals 622 (e.g., bluetooth signals) from a music source 625 such as a smartphone, radio or computer that sends the music signals 622.

In response to the music signals, the system 600 can apply stimulus from the actuator regions to the targeted tissue with the stimulus parameters being controlled and modulated by the control unit 145 in response to an 'aspect' of the music, or in response to multiple aspects of the music. The 'aspects' of the music that may be used by a controller algorithm to modulate stimulus parameters can be pitch, beat, rhythm, tempo, loudness and/or timbre. In one variation, the stimulus parameters that can be modulated in response to music are frequency and/or amplitude of motion of the actuator region as described previously. In another variation, the amplitude of suction through a surface of the actuator region (and the resultant tissue stabilization and/or stretching) can be modulated in response to the music signal 622. An additional system variation is shown below in FIGS. 16A-16C, 17, 18A and 18B that provides subsystems for incorporating suction ports into an actuator surface.

FIG. 15 schematically depicts another variation of a stimulus system 600 which again includes a glove-like stimulus device 605 similar to the type illustrated in FIG. 9, with the device 605 having actuatable regions 615 *a* and 615 *b*. The actuatable regions again can be fluidic chambers 150 (see FIGS. 11A-11B) within in a very thin elastomer wall as described previously or can be an eccentric rotating mass vibration mechanism, a linear resonant actuator, a piezoelectric actuator or an electro-active polymer actuator. The proximal part 620 of the device 605 again carries, or is coupled to, a drive unit 110 for driving the actuator regions 615 *a* and 615 *b*, a control unit 145 and a memory unit 240 as described above. In this variation, the control unit 145 is adapted to receive signals 622 (e.g., bluetooth signals) from a music source 625 such as a smartphone, radio or computer that sends the music signals 622.

Figure 17:
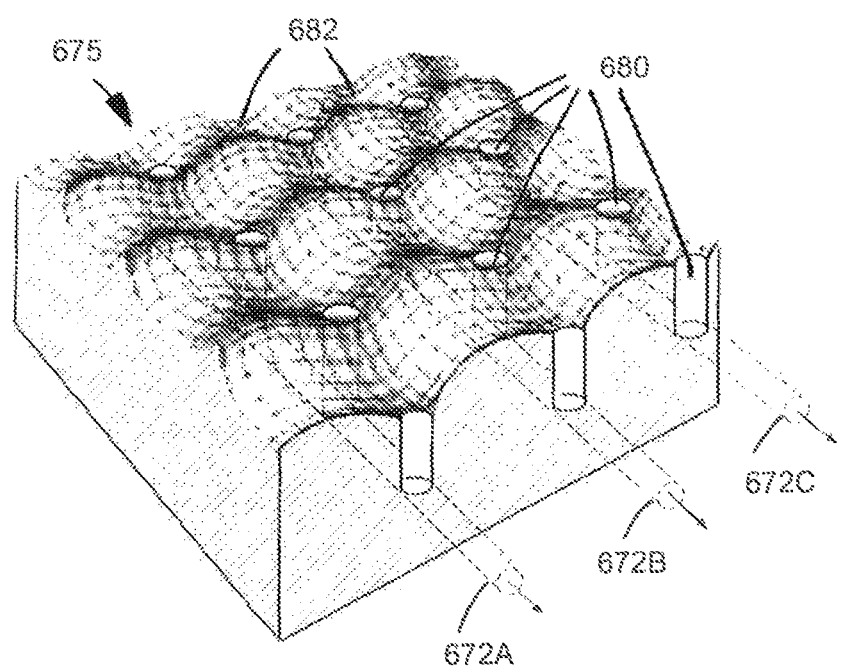
FIG. 17 is an enlarged sectional perspective view of the undulating actuator surface of FIG. 16B showing suction ports and flow channels therein.

Now referring to FIGS. 16A-18B, another system variation 650 is shown that includes suction functionality integrated into a surface layer of an actuator region. More in particular, FIG. 16A shows a wearable device 655 that is similar to previous embodiments with this variation having a single actuatable region 660 but it should be appreciated that multiple actuatable regions are possible as in previous embodiments. The proximal part 664 of the device 650 again includes or is connected to a drive unit 110 for actuating the actuator region 660, a control unit 145 and a memory unit 240 as in previous variations. In this variation, the proximal part 664 of the device 650 also carries a motor driven pump or vacuum source 670 that communicates with a flow channel 672 in the wearable device 655 that extends to the actuator region 660. FIG. 16B is a sectional view of one variation of an actuator region 660 which has a channeled or undulating surface 675 that is shown in a greatly enlarged cut-away view in FIG. 17. As can be seen in FIG. 17, the undulating surface 675 has aspiration ports 680 in the troughs 682 of the actuator surface. Each of the ports 680 communicates with an interior flow channel branch 672a-672c that extends back to the flow channel 672 and to the suction source 670. The undulations can have a height ranging from about 0.5 mm to 5.0 mm with a similar range from peak to peak of the undulations.

In the variation of actuator shown in FIGS. 16A and 17, it can be seen that at least one mechanical actuator or vibration mechanism 690 is carried inward of the undulating surface 675 and inward of the flow channel branches 672a-672c and ports 680. The actuator is a linear resonant actuator, an eccentric rotating mass vibration mechanism, or a piezoelectric actuator. It also would be possible to have a fluidic actuator as described above disposed in a layer below the flow channel branches 672a-672c and ports 680. FIG. 16C illustrates another similar actuator region 660' that has two actuators or vibrating mechanisms 690' that have different orientations relative to one another, which again can be a linear resonant actuator, an eccentric rotating mass vibration mechanism, or a piezoelectric actuator. Multiple actuators that apply stimulus in different vectors is believed to be useful for the stimulation of targeted tissue from different angles which can synchronized to be in unison or can be sequential. The periphery of the undulating surface 675 can be planar as in FIG. 16A, convex as in FIG. 16B or concave depending on the device and targeted tissue, and in general, the targeted soft tissue can conform to shape of the undulating surface 675.

Figure 18A:
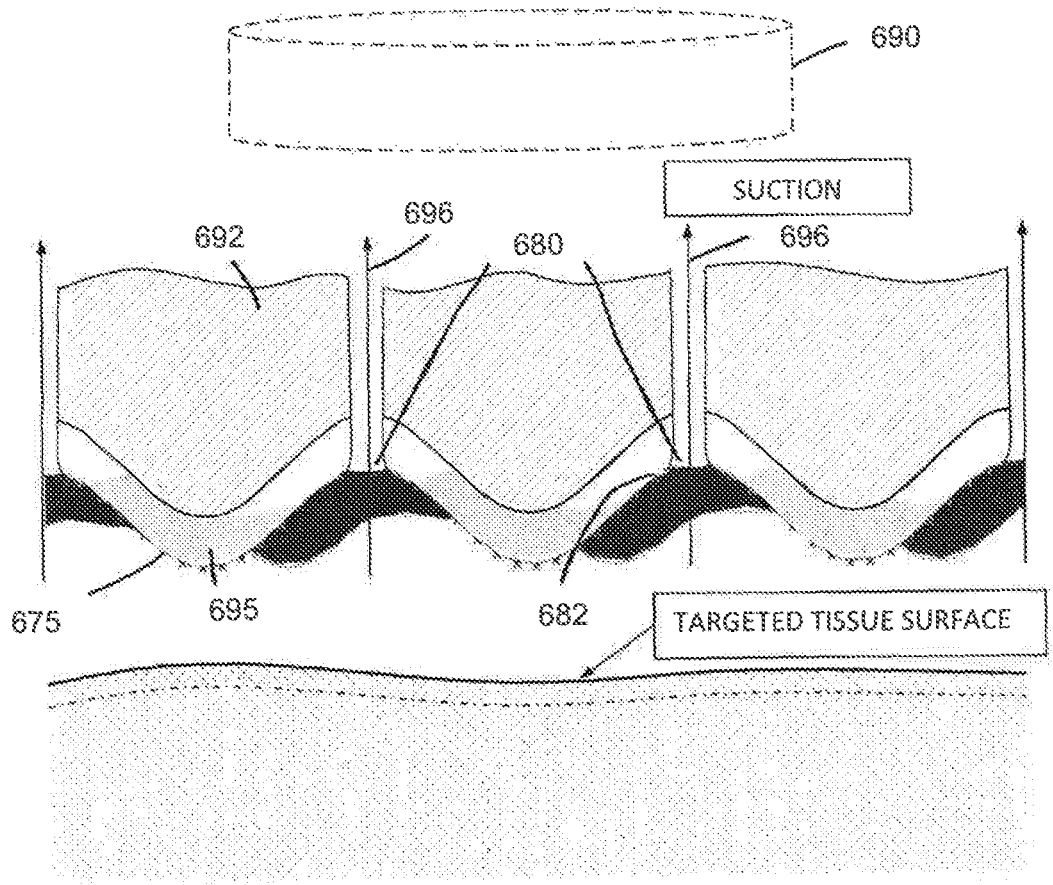
FIG. 18A illustrated a step in a method of the invention wherein a user is (i) moving the undulating actuator surface of FIG. 17 into close proximity to targeted tissue and (ii) activating the suction source to cause aspiration through the ports.
Figure 18B:
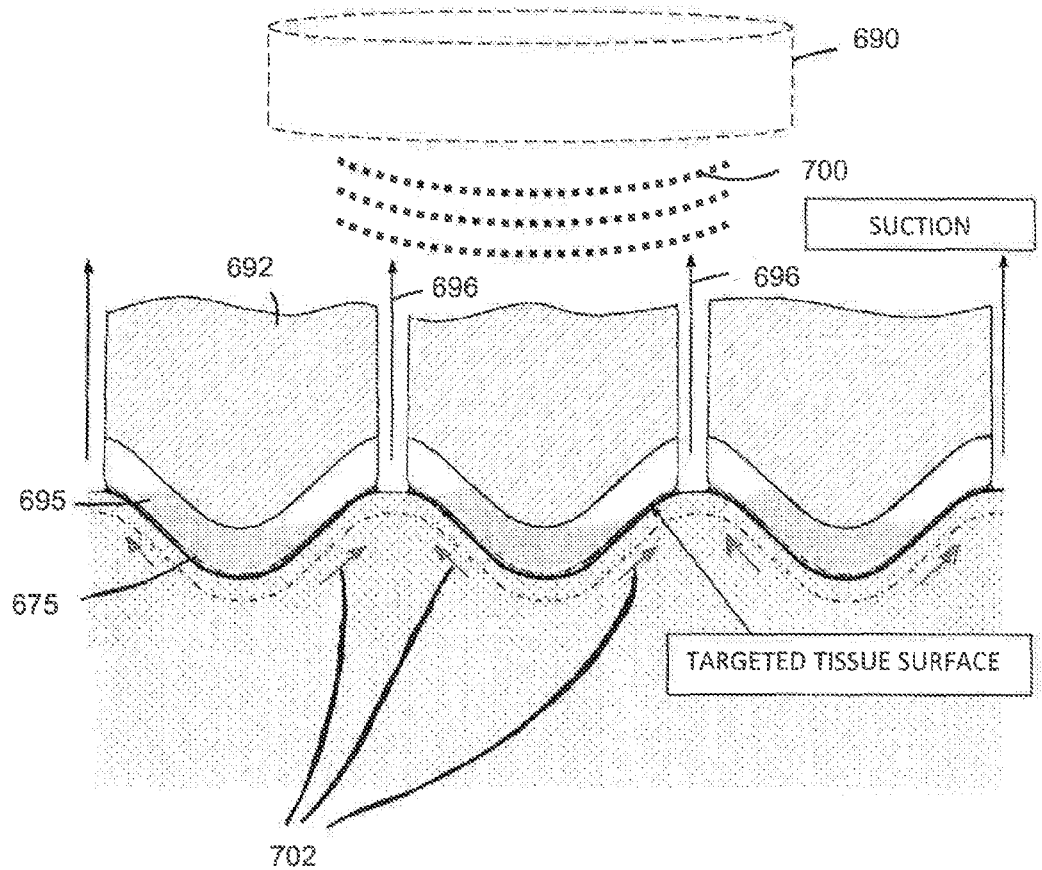
FIG. 18B illustrates a subsequent step with the suction source engaging and suctioning the targeted tissue against the undulating actuator surface together with activating the actuator to apply stimulus to the tensioned and stretched tissue.

FIGS. 18A and 18B are greatly enlarged sectional views of the undulating surface 675 of a stimulus device in use and illustrate a method of engaging the targeted tissue. FIG. 18A shows the undulating surface 675 in close proximity to a target tissue surface. In this variation, the undulating surface 675 has an inner layer 692 of an elastomeric material and surface layer 695 of a very low modulus elastomer that can conform to any tissue surface. In various embodiments, the surface layer 695 can be fluid impermeable and hydrophilic. FIG. 18A shows the suction source 670 being actuated with aspiration forces indicated by arrows 696.

FIG. 18B shows the undulating surface 675 moved into contact with the targeted tissue and the suction forces indicated by arrows 696 pulling the tissue surface into the undulations. This has the effect stabilizing the tissue to better receive the stimulation forces indicated at 700 from the actuator 690. Further, the tissue surface will be somewhat stretched and tensioned in the direction of arrows 702 in FIG. 18B which can make receptors in the targeted tissue more receptive to stimulation. Further, the suction forces applied to the targeted tissue can increase blood flow to the engaged tissue which can be important in a stimulation episode. In general, a method of stimulus for promoting female well-being comprises engaging a targeted surface of female sensory tissue with a device worn on a human hand to thereby stretch or tension the targeted surface, and applying stimulus from the device surface to said tensioned tissue surface to stimulate sensory tissue. The method includes applying suction to the targeted tissue surface through a plurality of flow passageways and ports distributed over the device surface. The method further includes applying the stimulation forces in unison or sequentially from different actuators along different vectors. Further, the stimulation forces can be modulated by the subject and her partner interactively as described in previous embodiments.

In another variation, the actuator surface 675 as in FIGS. 16A-18B can be fabricated with a second set of flow pathways and ports for providing fluid inflows to the targeted tissue from a fluid reservoir 710 in the wearable device 655 (see FIG. 15). A fluid for delivery through the system can be a lubricating fluid, a cooled fluid, a heated fluid, an aromatic fluid, a hydrating fluid, a therapeutic fluid or a pharmacologic fluid.

A number of embodiments of the invention have been described. Nevertheless, it will be understood that various modifications may be made without departing from the spirit and scope of the invention.

What is claimed is:

1. A method of controlled stimulation of tissue by both a first individual and a second individual, the method comprising:
   contacting sensory tissue of the first individual with a fluidic actuator comprising an expandable chamber having a first volume in a first configuration and a second volume in a second configuration, wherein the first volume in the first configuration is less than the second volume in the second configuration; and
   actuating the fluidic actuator with a plurality of control signals provided contemporaneously, wherein the plurality of control signals includes at least a first control signal generated by the first individual and a second control signal generated by the second individual.

2. The method of claim 1 wherein a controller harmonizes the first and second control signals.

3. The method of claim 1 wherein the fluidic actuator is disposed in a wearable device.

4. The method of claim 1, where the second individual generates the second control signal at a location removed from the first individual.

5. The method of claim 1, wherein the fluidic actuator is disposed in a glove-shaped body configured for wearing at least in part on a finger or hand, and wherein the method of claim 1 further comprises:
   actuating the fluidic actuator with control signals provided by a sensor in the glove-shaped body that senses movement of a finger or hand of the second individual.

6. The method of claim 5, wherein said movement of the finger or hand is adapted to adjust an actuation parameter over a range of actuation.

7. The method of claim 6, wherein the actuation parameter is at least one of amplitude and frequency.

8. The method of claim 1, further comprising filling the expandable chamber with gas or liquid.

9. The method of claim 1, wherein the fluidic actuator is proximate an elastomeric portion of a glove-shaped body worn by the second individual's hand wherein the elastomeric portion is substantially thin to thus allow sensory forces to be applied to both the first individual's sensory tissue and the second individual's hand.

10. The method of claim 9, wherein the elastomeric portion has a thickness of less than 2 mm, less than 1 mm or less than 0.5 mm.

11. The method of claim 1, wherein a fluid in the fluid actuator is cooled below a body temperature.

12. The method of claim 11, wherein the fluidic actuator is part of a wearable device, and wherein the fluid is cooled by a remote cooling mechanism or a cooling mechanism part of the wearable device.

13. The method of claim 1, further comprising:
   applying stimulus to the first individual to induce frisson, wherein the stimulus is provided by a wearable system that is configured to provide tactile stimulus, audible stimulus and/or non-ambient temperature stimulus to sensory tissue of the first individual.

14. The method of claim 13, wherein a system controller harmonizes the tactile, audible and/or temperature stimulus.

15. The method of claim 1, further comprising:
applying stimulus to the first individual, wherein the stimulus is provided by a system including a first wearable device worn by the first individual and a second wearable device worn by the second individual, and wherein the first wearable device and the second wearable device are configured to transmit signals therebetween to apply tactile stimulus, audible stimulus and/or non-ambient temperature stimulus.

16. The method of claim 1, further comprising:
engaging a targeted surface of sensory tissue with a portion of a glove-shaped device in contact with the targeted surface configured to tension the targeted surface; and
applying stimulus from the glove-shaped device to said targeted surface.

17. The method of claim 16, wherein the engaging step includes applying suction to the targeted surface through a plurality of flow passageways distributed over the portion of the glove-shaped device.

18. The method of claim 1, further comprising:
engaging a targeted female sensory tissue with a portion of a glove-shaped device;
applying stimulus from a second actuator to the targeted female sensory tissue, wherein stimulus parameters are controlled by a controller; and
modulating the stimulus parameters with controller algorithms that are responsive to at least one aspect of music.

19. The method of claim 18, wherein the stimulus parameters are at least one of frequency and amplitude of motion.

20. The method of claim 18, wherein the at least one aspect of music is selected from the group of pitch, beat, rhythm, tempo, loudness and timbre.

* * * * *